United States Patent
Arai et al.

[11] Patent Number: 6,118,842
[45] Date of Patent: Sep. 12, 2000

[54] X-RAY IMAGING APPARATUS

[75] Inventors: Yoshinori Arai, Tokyo; Keisuke Mori, Kyoto; Masakazu Suzuki, Kyoto; Akifumi Tachibana, Kyoto, all of Japan

[73] Assignee: J. Morita Manufacturing Corporation, Kyoto, Japan

[21] Appl. No.: 08/987,218

[22] Filed: Dec. 9, 1997

[30] Foreign Application Priority Data

Dec. 10, 1996 [JP] Japan .................................. 8-330066
Nov. 14, 1997 [JP] Japan .................................. 9-313963

[51] Int. Cl.⁷ ....................................................... A61B 6/14
[52] U.S. Cl. ................................. 378/39; 378/38; 378/901
[58] Field of Search .................................. 378/38, 39, 40, 378/901

[56] References Cited

U.S. PATENT DOCUMENTS

| | | |
|---|---|---|
| 5,058,147 | 10/1991 | Nishikawa et al. . |
| 5,093,852 | 3/1992 | Nishikawa et al. . |
| 5,224,140 | 6/1993 | Virta et al. ................................. 378/38 |
| 5,293,312 | 3/1994 | Waggener ................................. 378/14 |
| 5,793,838 | 8/1998 | Kovacs ..................................... 378/39 |

FOREIGN PATENT DOCUMENTS

| | | |
|---|---|---|
| S55-1053 | 1/1980 | Japan . |
| H7-136158 | 5/1995 | Japan . |

*Primary Examiner*—David V. Bruce
*Attorney, Agent, or Firm*—Koda & Androlia

[57] ABSTRACT

An object of the invention is to provide a dual-purpose X-ray imaging apparatus capable of partial CT imaging in addition to panoramic tomographic imaging. Another object of the invention is to provide a dedicated partial X-ray CT imaging apparatus. An X-ray imaging apparatus comprises an X-ray source 28 which irradiates an object with X-rays; an image sensor 38 which detects X-rays having passed through the object; a support arm 24 which supports the X-ray source 28 and the image sensor 38; and a plurality of motors for moving the support arm 24. These motors move the X-ray source 28 and image sensor 38 along a CT image formation locus in the CT mode, and the X-ray source 28 and the image sensor 38 along a panoramic image formation locus in the case of the panorama mode.

15 Claims, 26 Drawing Sheets

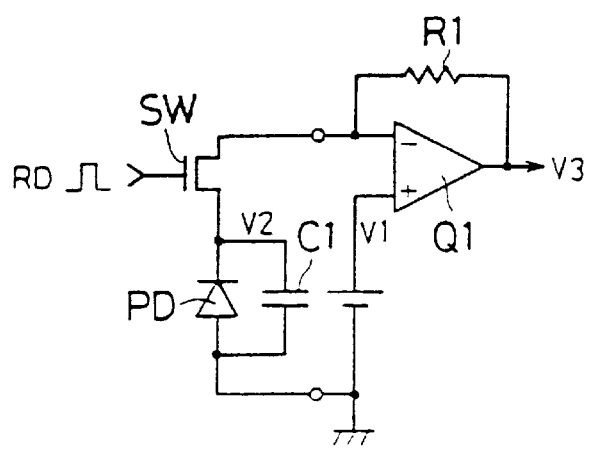
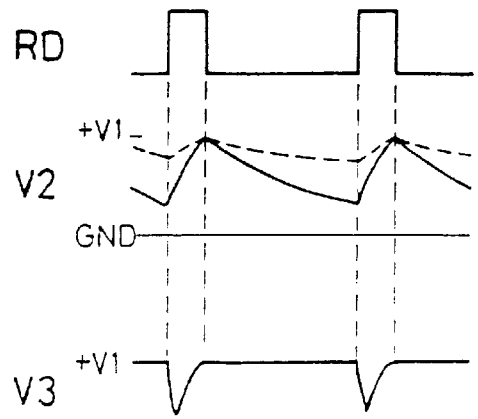
FIG.10A  FIG.10B
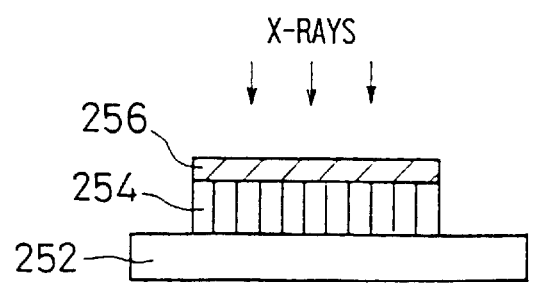
FIG.11

X-RAY IMAGING APPARATUS

BACKGROUND OF THE INVENTION

1. Field of the Invention

The present invention relates to an X-ray imaging apparatus which takes an image of an object such as a head of a human body along a desired tomographic plane.

2. Description of the Related Art

In the field of the dental diagnosis, conventionally, an X-ray panoramic imaging apparatus which takes a tomographic image along the curve of a dental arch is known as disclosed in, for example, Japanese Examined Patent Publication JP-B2 55-1053(1980). In such an X-ray panoramic imaging apparatus, an X-ray source and X-ray imaging means which is opposed to the X-ray source are moved along a desired locus, so that a curved-face tomographic image along the curve of the dental arch is obtained.

In the field of medical diagnosis, there is known an X-ray CT (computed tomographic) imaging apparatus which takes a tomographic image of an arbitrary site of a human body. In such an X-ray CT imaging apparatus, an X-ray source and X-ray imaging means which is opposed to the X-ray source are revolved in a predetermined direction, and an obtained image signal is processed by a computer, so that a CT image which is a section view at an arbitrary angle of an arbitrary site such as the head or the trunk can be obtained.

An X-ray panoramic imaging apparatus of the prior art is dedicated to the X-ray panoramic imaging, and hence can obtain only a panoramic tomographic image. The X-ray CT imaging apparatus of the prior art is used for taking a tomographic image of a large portion of the human body such as the head or the trunk, and dedicated to the CT imaging, with the result that it can obtain only a CT image.

In the field of dental diagnosis, if data such as the thickness of the jawbone are previously known prior to an implant operation or the like, the operation can be easily performed. Therefore, it is requested to take a partial CT image of the site to be subjected to the implant operation, by using an X-ray CT imaging apparatus. However, an X-ray panoramic imaging apparatus cannot take a CT image of such a site. An X-ray CT imaging apparatus of the prior art is bulky and expensive, and has a problem that the exposure dose is large. When the exposure dose is large during an imaging process, the allowable number of imaging processes is restricted. Such restriction may adversely affect the diagnosis.

When an X-ray CT imaging apparatus which is entirely independent from an X-ray panoramic imaging apparatus is used, the space for installing the X-ray CT imaging apparatus is problematic.

Recently, an X-ray imaging apparatus which can conduct both the X-ray panoramic imaging and the flat tomographic imaging is proposed (Japanese Unexamined Patent Publication JP-A 7-136158(1995)). In the apparatus, however, the flat tomographic plane must be determined before the imaging process, and the tomographic plane cannot be changed after the imaging process. Furthermore, the apparatus cannot obtain an image of a tomographic plane which intersects with the flat tomographic plane.

When the X-ray imaging is to be conducted, particularly, when the X-ray CT imaging is to be conducted on a local site, it is important to hold the site to be imaged of the object, an X-ray source, and X-ray imaging means in predetermined positional relationships. If they fail to be held in the predetermined positional relationships, a satisfactory X-ray image cannot be obtained.

SUMMARY OF THE INVENTION

It is an object of the invention to provide an X-ray imaging apparatus which can conduct a partial CT imaging in addition to a panoramic tomographic imaging.

It is another object of the invention to provide an X-ray imaging apparatus which can conduct a local CT imaging.

It is a further object of the invention to provide an X-ray imaging apparatus which, during a partial CT imaging process, an object, X-ray source, and X-ray imaging means can be held in predetermined positional relationships.

Firstly, an invention relating to an X-ray imaging apparatus capable of conducting a partial X-ray CT imaging and an X-ray panoramic imaging will be described.

A first aspect of the invention provides an X-ray imaging apparatus comprising: an X-ray source for generating X-rays; X-ray imaging means for detecting X-rays having passed through an object; supporting means for supporting the X-ray source and the X-ray imaging means so that the X-ray source and the X-ray imaging means are opposed to each other across the object; an apparatus frame for supporting the supporting means; and moving means for moving the supporting means with respect to the apparatus frame, the apparatus further comprising mode switching means for switching between a CT mode in which a partial CT image is generated, and a panorama mode in which a panoramic tomographic image is generated, and, when the CT mode is selected by the mode switching means, the moving means moves the X-ray source and the X-ray imaging means along a CT image formation locus during a partial CT imaging process, and when the panorama mode is selected by the mode switching means, the moving means moves the X-ray source and the X-ray imaging means along a panoramic image formation locus during a panoramic imaging process.

In the X-ray imaging apparatus, the imaging mode is selected by the mode switching means. When the CT mode is selected by the mode switching means, the moving means moves the X-ray source and the X-ray imaging means along the CT image formation locus. Therefore, the partial X-ray CT imaging can be conducted. By contrast, when the panorama mode is selected by the mode switching means, the moving means moves the X-ray source and the X-ray imaging means along the panoramic image formation locus. Therefore, the X-ray panoramic imaging can be conducted. In this way, the imaging mode is selected by the mode switching means, whereby the selected X-ray imaging can be conducted.

A second aspect of the invention is characterized in that, the CT image formation locus is a locus in which the supporting means is rotated about a rotation axis of the supporting means without moving the rotation axis, the panoramic image formation locus is a locus in which the rotation axis of the supporting means is moved along an envelope and the supporting means is rotated about the rotation axis as required, and, when the X-ray source and the X-ray imaging means are moved along the panoramic image formation locus, X-rays emitted from the X-ray source toward the X-ray imaging means are irradiated in a direction substantially perpendicular to a dental arch.

According to the invention, since the moving means rotates the supporting means about the rotation axis of the supporting means during a partial CT imaging process, a desired partial X-ray CT imaging can be conducted. During a panoramic imaging process, the moving means moves the rotation axis of the supporting means along an envelope, and rotates the supporting means about the rotation axis as required. Therefore, X-rays emitted from the X-ray source toward the X-ray imaging means are directed in a direction which is substantially perpendicular to the dental arch, and a desired panoramic imaging can be conducted.

A third aspect of the invention is characterized in that the apparatus further comprises movement controlling means for controlling the moving means, and the movement controlling means controls an operation of the moving means so that in the CT mode the X-ray source and the X-ray imaging means are moved along the CT image formation locus, and in the panorama mode the X-ray source and the X-ray imaging means are moved along the panoramic image formation locus.

According to the invention, since the movement controlling means controls the operation of the moving means so that, in the CT mode, the X-ray source and the X-ray imaging means are moved along the CT image formation locus, and, in the panorama mode, the X-ray source and the X-ray imaging means are moved along the panoramic image formation locus, when the imaging mode is selected by the mode switching means, therefore, the selected X-ray imaging can be automatically conducted.

A forth aspect of the invention is characterized in that, the moving means comprises: an X-axis control motor for moving the supporting means in an anteroposterior direction; a Y-axis control motor for moving the supporting means in a lateral direction; and a rotation control motor for rotating the supporting means about a rotation axis, and the movement controlling means controls an operation of the rotation control motor in the CT mode, and simultaneously controls operations of the X-axis control motor, the Y-axis control motor, and the rotation control motor in the panorama mode.

In the X-ray imaging apparatus, since, in the CT mode, the movement controlling means controls an operation of the rotation control motor, the X-ray source and the X-ray imaging means are moved along the CT image formation locus. Since, in the panorama mode, the movement controlling means simultaneously controls operations of the X-axis control motor, the Y-axis control motor, and the rotation control motor, the X-ray source and the X-ray imaging means are moved along a panoramic image formation locus.

A fifth aspect of the invention is characterized in that the X-ray imaging means detects the X-ray from the X-ray source and outputs an image signal, the apparatus further comprises, in relation to the X-ray imaging means, image signal processing means for forming a tomographic image on the basis of the image signal, and the image signal processing means generates, in the CT mode, a partial CT image on the basis of the image signal from the X-ray imaging means, and, in the panorama mode, a panoramic tomographic image on the basis of the image signal from the X-ray imaging means.

According to the invention, the X-ray imaging means detects the X-rays from the X-ray source as an image signal, and the image signal processing means for processing the image signal generates, in the CT mode, a partial CT image on the basis of the image signal from the X-ray imaging means, and, in the panorama mode, a panoramic tomographic image on the basis of the image signal from the X-ray imaging means. When the imaging mode is selected by the mode switching means, therefore, the image signal processing means conducts an image processing corresponding to the selected mode and a tomographic image corresponding to the selected imaging mode can be automatically obtained.

A sixth aspect of the invention is characterized in that, the apparatus further comprises, in relation to the movement controlling means and the image signal processing means, process information storing means for storing CT process information for obtaining the partial CT image and panorama process information for obtaining the panoramic tomographic image; when the CT mode is selected by the mode switching means, the CT process information of the process information storing means is selected, the movement controlling means moves the X-ray source and the X-ray imaging means along the CT image formation locus on the basis of the CT process information, and the image signal processing means generates the partial CT image on the basis of the image signal from the X-ray imaging means; and, when the panorama mode is selected by the mode switching means, the panorama process information of the process information storing means is selected, the movement controlling means moves the X-ray source and the X-ray imaging means along the panoramic image formation locus on the basis of the panorama process information, and the image signal processing means generates the panoramic tomographic image on the basis of the image signal from the X-ray imaging means.

According to the invention, the process information storing means stores CT process information for obtaining a partial CT image, and panorama process information for obtaining a panoramic tomographic image. In the case of the CT mode, the CT process information is selected, the X-ray source and the X-ray imaging means are moved along the CT image formation locus on the basis of the CT process information, and the image signal processing means generates a partial CT image on the basis of the image signal from the X-ray imaging means. By contrast, in the case of the panorama mode, the panorama process information is selected, the X-ray source and the X-ray imaging means are moved along the panoramic image formation locus on the basis of the panorama process information, and the image signal processing means generates a panoramic tomographic image on the basis of the image signal from the X-ray imaging means. When the imaging mode is selected by the mode switching means, therefore, an image processing corresponding to the selected mode is conducted and a tomographic image corresponding to the selected mode can be obtained.

A seventh aspect of the invention is characterized in that, the apparatus further comprises primary slit means for restricting a range of X-rays emitted from the X-ray source toward the object, and secondary slit means for restricting a range of X-rays entering the X-ray imaging means, the primary slit means comprises primary slit switching means for switching over a primary CT slit and a primary panorama slit; the secondary slit means comprises secondary slit switching means for switching between a secondary CT slit and a secondary panorama slit; when the CT mode is selected by the mode switching means, the primary CT slit is selected by the primary-slit switching means and the secondary CT slit is selected by the secondary slit switching means; and, when the panorama mode is selected by the mode switching means, the primary panorama slit is selected by the primary slit switching means and the secondary panorama slit is selected by the secondary-slit switching means.

According to the invention, when the CT mode is selected by the mode switching means, the primary CT slit is selected by the primary-slit switching means, and the secondary CT slit is selected by the secondary-slit switching means, in accordance with the selected CT mode. By contrast, when the panorama mode is selected by the mode switching means, the primary panorama slit is selected by the primary-slit switching means, and the secondary panorama slit is selected by the secondary-slit switching means. In this way, slits corresponding to the imaging mode selected by the mode switching means are selected by the primary and secondary slit means. Therefore, a selected desired tomographic image can be obtained.

A eighth aspect of the invention is characterized in that the apparatus further comprises object positioning means for positioning the object in an imaging region which is between the X-ray source and the X-ray imaging means, and positional relationships between the object positioning means, and the X-ray source and the X-ray imaging means are relatively adjustable in anteroposterior, lateral, and vertical directions.

In the X-ray imaging apparatus, since positional relationships between the object positioning means, and the X-ray source and the X-ray imaging means are relatively adjustable in anteroposterior, lateral, and vertical directions, the object positioning means can be positioned at a desired position with respect to the X-ray source and the X-ray imaging means.

A ninth aspect of the invention is characterized in that, the moving means includes a plane moving mechanism which supports the supporting means in a manner that the supporting means is movable with respect to the apparatus frame in anteroposterior and lateral directions, the object positioning means is mounted on the apparatus frame via an object position adjusting mechanism for supporting the object positioning means in a manner that the object positioning means is movable in vertical direction, and positional relationships between the object positioning means, and the X-ray source and the X-ray imaging means are adjusted by the plane moving mechanism and the object position adjusting mechanism in anteroposterior, lateral, and vertical directions.

In the X-ray imaging apparatus, since the relative positions between the object positioning means, and the X-ray source and the X-ray imaging means are adjusted by the plane moving mechanism in anteroposterior and lateral directions, and by the object position adjusting mechanism in vertical direction, the positional relationships between the two means can be adjusted by a relatively simple configuration.

A tenth aspect of the invention is characterized in that, positional relationships between the object positioning means, and the X-ray source and the X-ray imaging means in the CT mode are set on the basis of position information obtained from the panoramic tomographic image which is obtained in the panorama mode.

In the X-ray imaging apparatus, positional relationships between the object positioning means, and the X-ray source and the X-ray imaging means in the CT mode are set by using a panoramic tomographic image which is obtained in the panorama mode. In other words, a panoramic tomographic image is first taken. The panoramic tomographic image is observed, and then a site to be subjected to the partial X-ray CT imaging is set. On the basis of position information of a panoramic tomographic image corresponding to the specified region, the X-ray source and the X-ray imaging means are held in predetermined positional relationships with the object positioning means. Therefore, these components can be correctly positioned in predetermined positional relationships in a relatively easy manner.

An eleventh aspect of the invention is characterized in that, before and after the partial CT imaging process, the supporting means is positioned at a specific angular position where a line connecting the X-ray source and the X-ray imaging means laterally elongates.

In the X-ray imaging apparatus, before and after a partial CT imaging process, the supporting means is positioned at a specific angular position. When a partial CT imaging process is to be conducted, therefore, the patient can rearward move toward the imaging region with passing through a space between the X-ray source and the X-ray imaging means. After the imaging process, the patient can forward leave the imaging region with passing through the space between the X-ray source and the X-ray imaging means. In this way, the patient can easily move without being obstructed by the supporting means, the X-ray source, and the X-ray imaging means.

Hereinafter, an invention relating to a dedicated partial X-ray CT imaging apparatus which is dedicated to the partial X-ray CT imaging will be described.

A twelfth aspect of the invention provides a partial X-ray imaging apparatus comprising: an X-ray source for generating X-rays; X-ray imaging means for detecting X-rays having passed through an object; supporting means for supporting the X-ray source and the X-ray imaging means so that the X-ray source and the X-ray imaging means are opposed to each other across the object; an apparatus frame for supporting the supporting means so as to be rotatable about a rotation axis; and rotation driving means for rotating the supporting means with respect to the apparatus frame, wherein an imaging region according to the X-ray source and the X-ray imaging means is substantially positioned on an extension line of the rotation axis of the supporting means, and during a partial X-ray CT imaging process, rotation driving means rotates the supporting means in a predetermined direction about the rotation axis, and the X-ray source and the X-ray imaging means are revolved about the imaging region, thereby conducting a partial CT imaging of the object.

According to the invention, the imaging region where the partial X-ray CT imaging is to be conducted is substantially positioned on an extension line of the rotation axis of the supporting means. During the partial X-ray imaging process, the supporting means is rotated about the rotation axis, and the X-ray source and the X-ray imaging means are revolved about the imaging region. Therefore, the imaging region is restricted to a local region, and the partial CT imaging can be conducted on the local region.

Further, a thirteenth aspect of the invention is characterized in that the supporting means comprises a support arm which is supported by the apparatus frame so as to be rotatable about the rotation axis extending in a vertical direction, a first attaching portion which downwardly elongates is disposed at one end portion of the support arm, a second attaching portion which downwardly elongates is disposed at another end portion of the support arm, the X-ray source is attached to the first attaching portion, the X-ray imaging means is attached to the second attaching portion, and the imaging region is placed between the first attaching portion and the second attaching portion of the support arm.

According to the invention, the support arm is supported so as to be rotatable about the rotation axis extending in the vertical direction, the X-ray source is attached to the first attaching portion disposed at one end portion of the support arm, and the X-ray imaging means is attached to the second attaching portion disposed at the other end portion of the support arm. Therefore, the imaging region is positioned between the first attaching portion and the second attaching portion of the support arm, so that the partial X-ray CT imaging can be conducted in a condition that, for example, the patient of the object keeps standing.

A fourteenth aspect of the invention is characterized in that, before and after the partial CT imaging process, the support arm is positioned at a specific angular position where a line connecting the X-ray source and the X-ray imaging means laterally elongates.

In the partial X-ray CT imaging apparatus, before and after a partial CT imaging process, the support arm is positioned at a specific angular position. At the specific angular position, the line connecting the X-ray source and the X-ray imaging means laterally elongates. Before and after an imaging process, therefore, the patient can forward or rearward move toward the imaging region with passing through a space between the X-ray source and the X-ray imaging means.

A fifteenth aspect of the invention is characterized in that, the X-ray source is provided with primary slit means, X-rays emitted from the X-ray source are irradiated in a cone-like shape or a pyramid-like shape through the primary slit means toward the imaging region, and the imaging region has a spherical or cylindrical shape which is substantially centered at the rotation axis of the supporting means.

According to the invention, X-ray emitted from the X-ray source are caused to irradiate the imaging region in a cone-like or pyramid-like shape by the function of the primary slit means, thereby forming the imaging region into a spherical or cylindrical shape which is substantially centered at the rotation axis of the supporting means. As compared with the prior art, therefore, the range of the imaging region is smaller and the apparatus is suitable as a partial X-ray CT imaging apparatus which conducts local CT imaging in the dental field.

A sixteenth aspect of the invention is characterized in that, object positioning means for positioning the object in the imaging region which is between the X-ray source and the X-ray imaging means is disposed, the object positioning means is mounted on the apparatus frame via an object position adjusting mechanism, and the object positioning means is made positionally adjustable with respect to the apparatus frame by the object position adjusting mechanism in anteroposterior, lateral, and vertical directions.

In the partial X-ray CT imaging apparatus, since the object positioning means is made positionally adjustable with respect to the apparatus frame by the object position adjusting mechanism in anteroposterior, lateral, and vertical directions, the object can be correctly positioned at a predetermined imaging position with respect to the X-ray source and the X-ray imaging means.

A seventeenth aspect of the invention is characterized in that, the apparatus further comprises: position storing means for storing object position information relating to positional relationships between the X-ray source and the X-ray imaging means, and the object positioning means; and position selecting means for selecting object position information stored in the position storing means, and the X-ray source, the X-ray imaging means, and the object positioning means are held in selected positional relationships on the basis of the object position information selected by the position selecting means.

According to the invention, object position information is stored in the position storing means, object position information selected by the position selecting means is read out, and the X-ray source, the X-ray imaging means, and the object positioning means are held to predetermined positional relationships on the basis of the read out object position information. Therefore, these components are automatically positioned in positional relationships which are selected by the position selecting means from plural sets of positional relationships which are preset.

An eighteenth aspect of the invention is characterized in that the supporting means comprises a light beam indicator for projecting a light beam toward the object positioning means, and the light beam indicator is disposed on the rotation axis of the supporting means.

According to the invention, the supporting means comprises the light beam indicator on the rotation axis in the case of the partial X-ray CT imaging, and the light beam indicator projects a light beam toward the object positioning means. When the object is positioned so as to coincide with the light beam projected from the light beam indicator, therefore, a site of the object onto which the light beam is projected can be positioned in the imaging region. As a result, the object, the X-ray source, and the X-ray imaging means can be held to predetermined positional relationships in a relatively easy manner.

BRIEF DESCRIPTION OF THE DRAWINGS

Other and further objects, features, and advantages of the invention will be more explicit from the following detailed description taken with reference to the drawings wherein:

FIG. 10A is a circuit diagram illustrating the operation principle of a MOS sensor used in the X-ray imaging apparatus of FIG. 1, and FIG. 10B is a timing chart of the MOS sensor;

FIG. 11 is a section view showing the structure of the MOS sensor of FIG. 10;

DETAILED DESCRIPTION OF THE PREFERRED EMBODIMENTS

Figure 1:
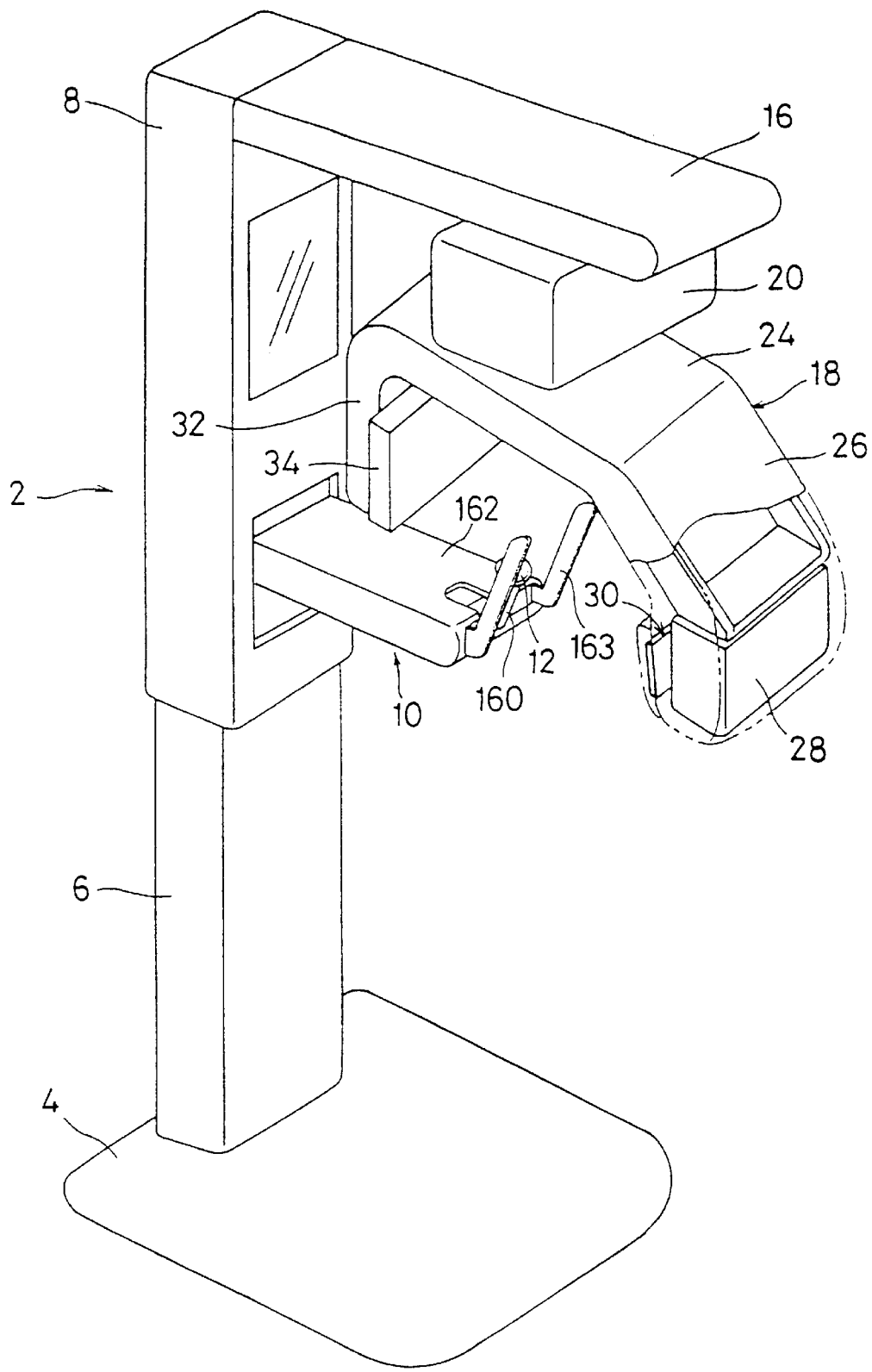
FIG. 1 is a partially cutaway perspective view showing a first embodiment of a dual-purpose X-ray imaging apparatus of the invention.

Now referring to the drawings, preferred embodiments of the invention are described below.

Figure 2:
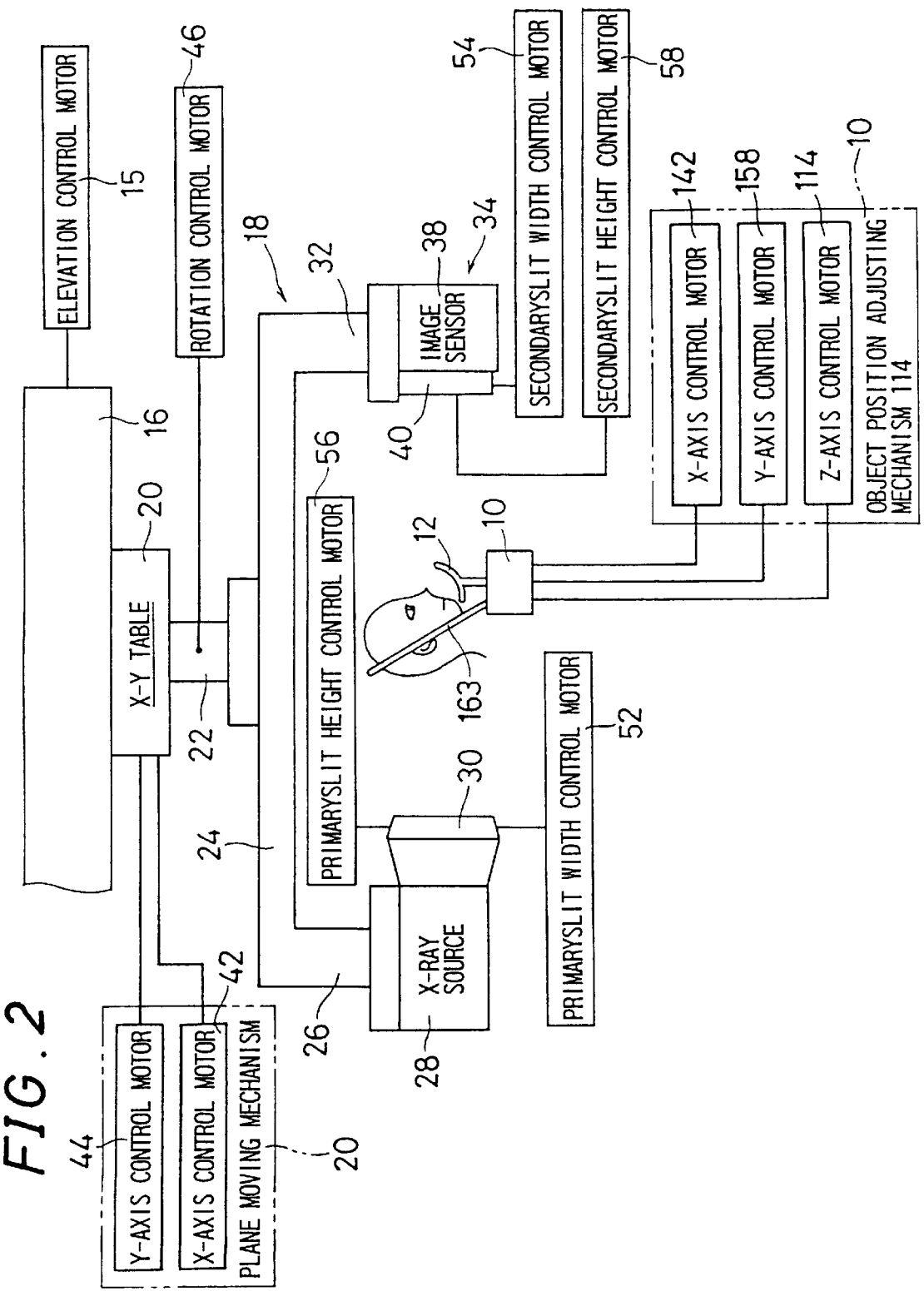
FIG. 2 is a block diagram showing an outline of the X-ray imaging apparatus of FIG. 1.
Figure 7:
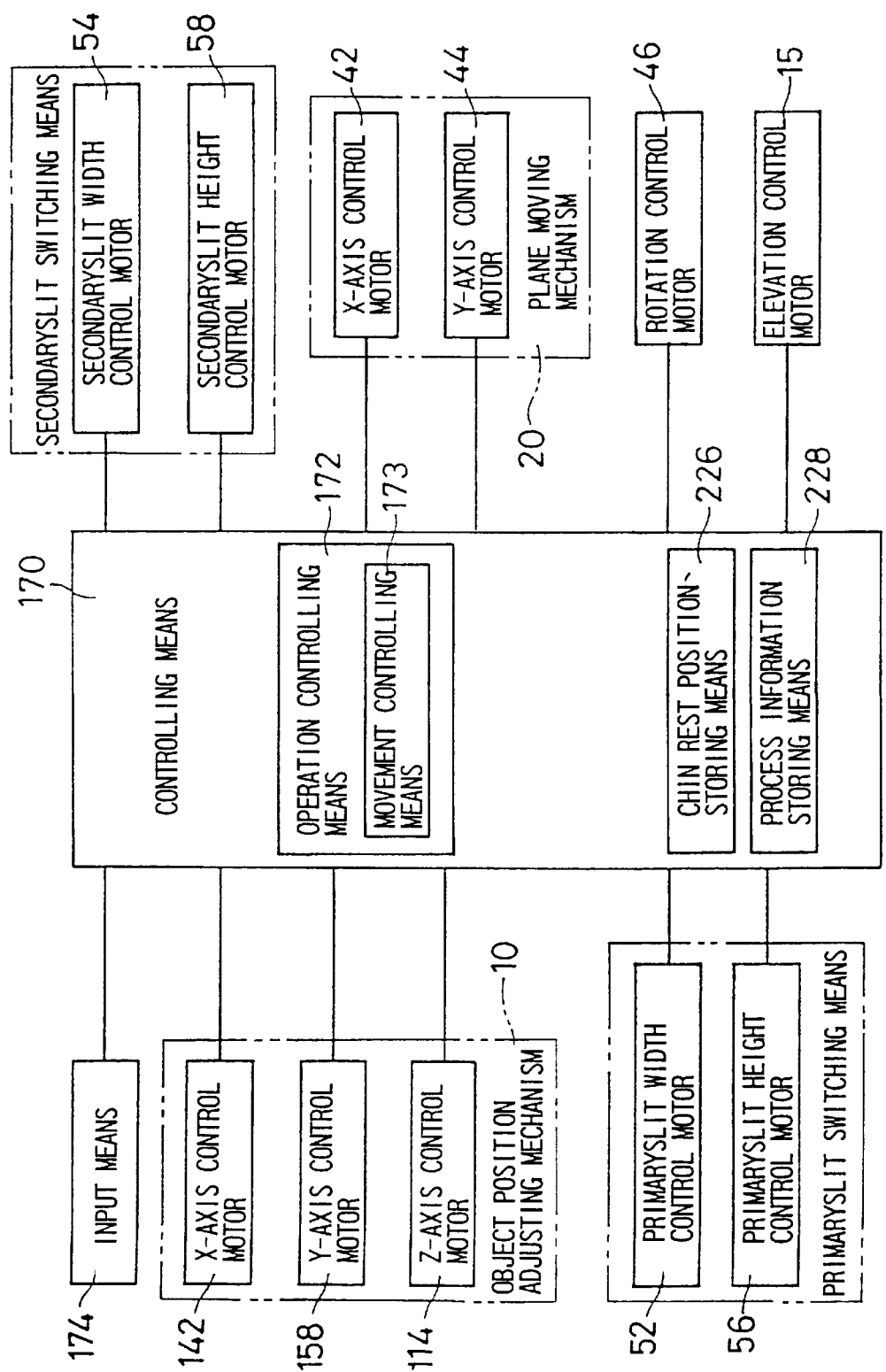
FIG. 7 is a block diagram showing a control system for various motors in the X-ray imaging apparatus of FIG. 1.

The X-ray imaging apparatus in FIG. 1 can conduct an X-ray panoramic imaging, in addition to an X-ray CT imaging for a local site. Referring to FIG. 1, an illustrated X-ray imaging apparatus comprises an apparatus frame 2. The apparatus frame 2 comprises a base 4 which is to be placed on a floor, a column 6 disposed on the base 4, and an elevator frame 8. The column 6 elongates from the base 4 in an upward direction which is substantially perpendicular to the base. The elevator frame 8 is mounted on the column 6 so as to be vertically movable, and vertically moved by an elevation control motor 15 (FIGS. 2 and 7). A chin rest 12 constituting object positioning means is mounted on the elevator frame 8 via an object position adjusting mechanism 10 so that the position of the chin rest 12 is arbitrarily set. A patient of an object stands on the base 4 and a chin of the patient is positioned on the chin rest 12. This positioning allows the site to be imaged, to be placed in an imaging area. Thereafter, an X-ray imaging is conducted on a predetermined site in the manner described later. The object position adjusting mechanism 10 and the configuration relating to the mechanism will be described later.

A horizontal arm 16 is disposed at the upper end portion of the elevator frame 8. The horizontal arm 16 elongates in the forward direction with respect to the apparatus or toward the right lower portion in FIG. 1. Supporting means 18 is mounted on the tip end portion of the horizontal arm 16. A plane moving mechanism 20 is interposed between the horizontal arm 16 and the supporting means 18. The plane moving mechanism 20 comprises an X-axis table which is movable in the anteroposterior direction (the direction from the right lower portion to the left upper portion in FIG. 1) with respect to the horizontal arm 16, and a Y-axis table which is movable in the lateral direction (the direction from the left lower portion to the right upper portion in FIG. 1) which is perpendicular to the anteroposterior direction. A rotation shaft 22 (see FIG. 2) is rotatably supported at a tip end portion of the plane moving mechanism 20. The supporting means 18 is mounted on the rotation shaft 22. Therefore, the center axis of the rotation shaft 22 constitutes the rotation axis of the supporting means 18, and the supporting means 18 is rotated about the rotation axis. The supporting means 18 has a support arm 24 which elongates in a predetermined direction. The middle portion of the support arm 24 is attached to the rotation shaft 22. A first attaching portion 26 which downwardly elongates is integrated with one end portion of the support arm 24. An X-ray source 28 and primary slit means 30 are disposed on the first attaching portion 26. The primary slit means 30 is placed in proximity to and in front of the X-ray source 28, and mounted on the X-ray source 28. A second attaching portion 32 which downwardly elongates is integrated with the other end portion of the support arm 24. An X-ray imaging unit 34 is mounted on the second attaching portion 32. The X-ray imaging unit 34 has X-ray imaging means for detecting X-rays emitted from the X-ray source 28. In the embodiment, the X-ray imaging means is configured by an image sensor 38 (see FIG. 2). The X-ray imaging unit 34 comprises secondary slit means 40 (see FIG. 2) which is placed in proximity to and in front of the image sensor 38.

As seen from FIG. 1, the object which is to be subjected to the X-ray imaging is positioned between the X-ray source 28 and the image sensor 38. The object is irradiated with X-rays emitted from the X-ray source 28. The primary slit means 30 restricts the width and height of X-rays emitted from the X-ray source 28, thereby preventing unnecessary X-rays from being emitted toward the object. X-rays having passed through the object are detected by the image sensor 38. As shown in FIG. 2, the secondary slit means 40 restricts the width and height of X-rays entering the image sensor 38, thereby preventing unnecessary X-rays from entering the image sensor 38. The slits of the primary and secondary slit means 30 and 40 which are selected in the X-ray imaging are similar in shape to each other and the slit of the secondary slit means 40 is preferably set to be slightly smaller than the shape of the irradiation beam irradiated via the primary slit means 30. In the X-ray imaging apparatus of the embodiment, both the partial CT imaging and the panoramic tomographic imaging can be conducted as described in detail later. In relation to this, the primary and secondary slit means 30 and 40 are configured so as to respectively constitute slit openings corresponding to the style of the selected tomographic imaging. The configurations of these means will be described later.

Next, referring to FIG. 2, an outline of the X-ray imaging apparatus will be further described. As described above, the plane moving mechanism 20 which is interposed between the horizontal arm 16 and the support arm 24 comprises the X-axis table and the Y-axis table. For example, the X-axis table is mounted on the horizontal arm 16 so as to be movable in the anteroposterior direction. In relation to the X-axis table, an X-axis control motor 42 which moves the table in the anteroposterior direction is disposed. The Y-axis table is mounted on the X-axis table so as to be movable in the lateral direction. In relation to the Y-axis table, a Y-axis control motor 44 which moves the table in the lateral direction is disposed. The rotation shaft 22 is rotatably supported on the Y-axis table. In relation to the rotation shaft 22, a rotation control motor 46 which rotates the rotation shaft and which constitutes rotating means is disposed. According to this configuration, the rotation of the X-axis control motor 42 enables the supporting means 18 to be moved in the anteroposterior direction with respect to the horizontal arm 16, i.e., the apparatus frame 2, the rotation of the Y-axis control motor 44 enables the supporting means 18 to be moved in the lateral direction with respect to the horizontal arm 16, and the rotation of the rotation control motor 46 enables the supporting means 18 to be rotated about the axis which vertically elongates, with respect to the horizontal arm 16. The X-axis control motor 42, the Y-axis control motor 44, and the rotation control motor 46 constitute moving means for moving the supporting means 18 as required in the partial CT imaging and the panoramic imaging.

Figure 3:
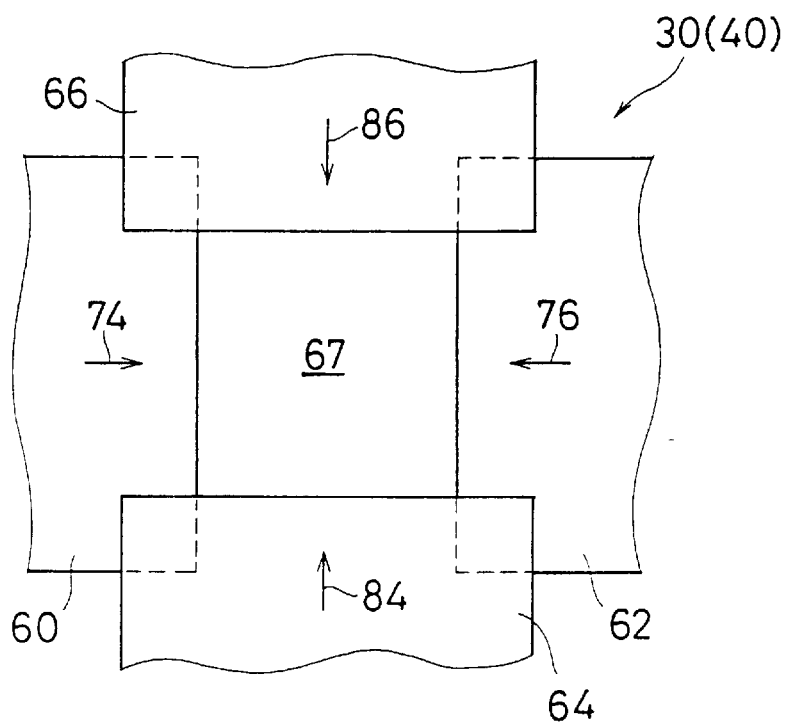
FIG. 3 is a front view showing main portions of primary (secondary) slit means in the X-ray imaging apparatus of FIG. 1.
Figure 4:
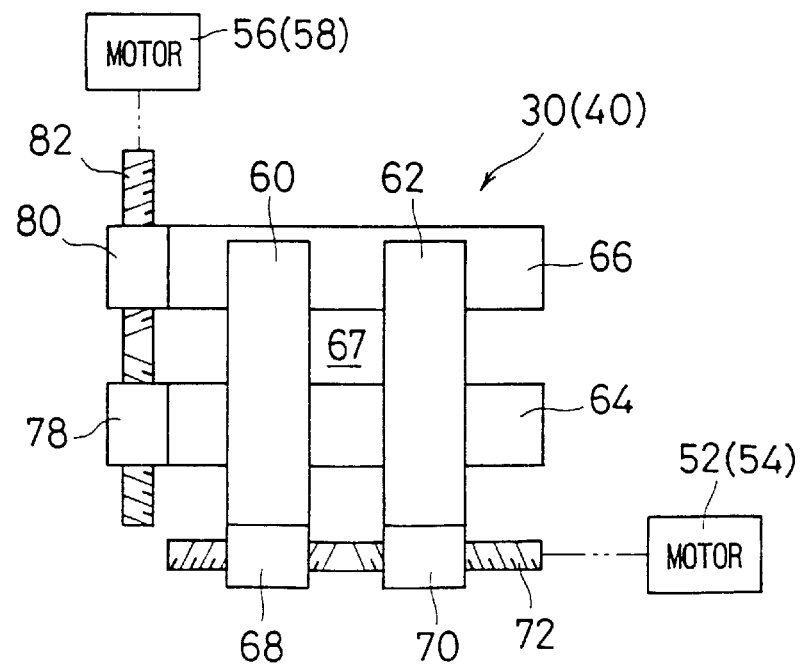
FIG. 4 is a front view showing the primary (secondary) slit means in the X-ray imaging apparatus of FIG. 1.

The primary and secondary slit means 30 and 40 comprise slit width control motors 52 and 54 for controlling the width of a slit, and slit height control motors 56 and 58 for controlling the height of a slit, respectively. In the embodiment, the primary and secondary slit means 30 and 40 are configured in a substantially identical manner. Referring to FIGS. 3 and 4, the configuration of the slit means will be specifically described. The primary (secondary) slit means 30 (40) comprises a pair of width shield members 60 and 62 which are arranged in the width direction, and a pair of height shield members 64 and 66 which are arranged in the height direction. The four shield members define a rectangular slit 67. Block-like members 68 and 70 are disposed at one end portions of the pair of width shield members 60 and 62. A screw shaft 72 passes through the block-like members 68 and 70. A pair of threaded portions which are threaded in opposite directions are formed on the screw shaft 72. One of the threaded portions is screwed with the block-like member 68, and the other threaded portion is screwed with the block-like member 70. The screw shaft 72 is drivingly coupled with the slit width control motor 52 (54). When the slit width control motor 52 (54) is rotated in a predetermined direction (or a direction opposite to the predetermined direction), the rotation of the screw shaft 72 causes the pair of width shield members 60 and 62 to approach each other (or separate from each other) in the directions indicated by arrows 74 and 76 (or directions respectively opposite to the directions indicated by the arrows 74 and 76), thereby reducing (or increasing) the width of the slit 67 which is defined by the pair of width shield members 60 and 62. Block-like members 78 and 80 are disposed at one end portions of the pair of height shield members 64 and 66. A screw shaft 82 passes through the block-like members 78 and 80. In the same manner as the screw shaft 72, a pair of threaded portions which are threaded in opposite directions are formed on the screw shaft 82. One of the threaded portions is screwed with the block-like member 78, and the other threaded portion is screwed with the block-like member 80. The screw shaft 82 is drivingly coupled with the slit height control motor 56 (58). When the slit height control motor 56 (58) is rotated in a predetermined direction (or a direction opposite to the predetermined direction), the rotation of the screw shaft 82 causes the pair of height shield members 64 and 66 to approach each other (or separate from each other) in the directions indicated by arrows 84 and 86 (or directions respectively opposite to the directions indicated by the arrows 84 and 86), thereby reducing (or increasing) the height of the slit 67 which is defined by the pair of height shield members 64 and 66.

Figure 5A:
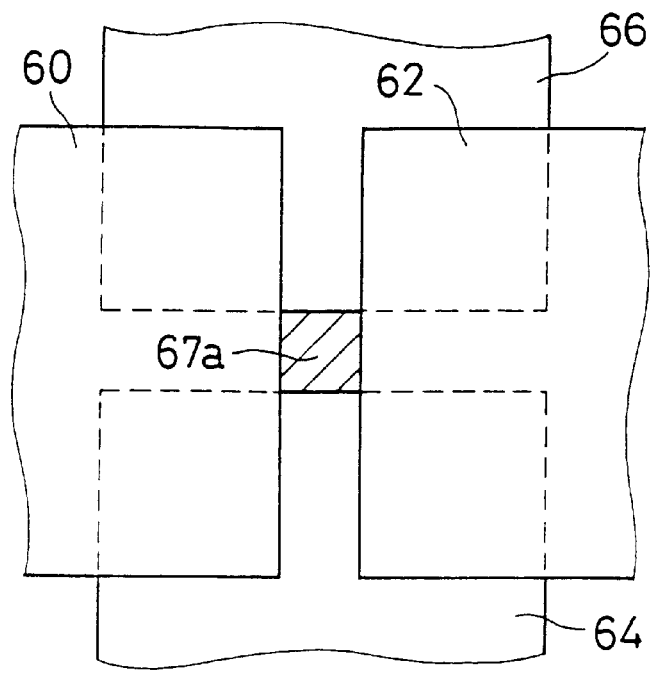
FIGS. 5A and 5B are views illustrating a slit opening of the primary (secondary) slit means.
Figure 5B:
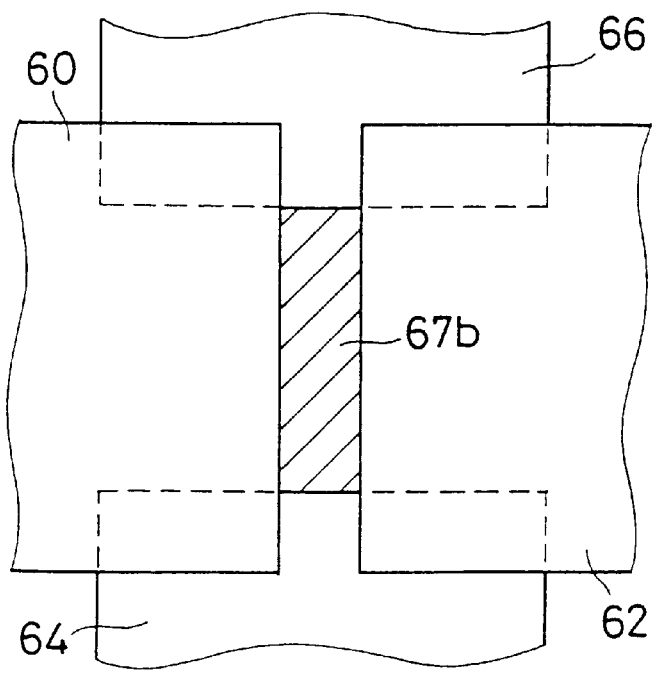

The operation of changing the size of the slit 67 by means of the slit width control motors 52 and 54 and the slit height control motors 56 and 58 is conducted in the following manner in accordance with the selected imaging mode. Referring to FIG. 5 (in FIG. 5, the slit opening is diagonally shaded), in the embodiment, when the partial CT imaging is selected, the primary and secondary slit means 30 and 40 define a small square slit 67a as shown in FIG. 5A. For example, the size of the slit 67a is set so that the slit has an edge of about 50 mm. In the case of the slit 67a, when X-rays from the X-ray source 28 pass through the slit 67a, the X-rays are caused to irradiate the imaging region in a quadrangular pyramid-like shape. When the panoramic tomographic imaging is selected, the primary and secondary slit means 30 and 40 define a rectangular square slit 67b which vertically elongates as shown in FIG. 5B. For example, the size of the slit 67b is set so that the slit has a width of about 6 mm and a height of about 150 mm. The operation of switching the slit 67 of the first and second slit means will be described later.

In the embodiment, the pair of width shield members 60 and 62, and the pair of height shield members 64 and 66 are moved so as to approach each other (or separate from each other). Alternatively, in the pair of width shield members 60 and 62, one of the members may be moved with respect to the other member, and, also in the pair of height shield members 64 and 66, one of the members may be moved with respect to the other member. A slit plate which has plural openings of a predetermined shape may be configured as each of the slit means 30 and 40, and the slit plate may be moved.

Next, referring to FIGS. 2 and 6, the object position adjusting mechanism 10 for positioning the chin rest 12 at a predetermined position, and the configuration relating to the mechanism will be described. The object position adjusting mechanism 10 comprises a guide frame 90 which is fixed in the elevator frame 8 of the apparatus frame 2. The guide frame 90 has a pair of side walls 92 (in FIG. 6, only one of them is shown) which are arranged with being separated from each other in a lateral direction (the direction perpendicular to the sheet in FIG. 6). A connecting wall 94 is disposed between the pair of side walls 92. A slender slot 96 which vertically elongates is formed in the middle area of the connecting wall 94. A first moving table 98 is mounted between the side walls 92 of the guide frame 90 so as to be movable in vertical directions. The first moving table 98 has a first table main unit 100 which is rectangular. A pair of rollers 102 are rotatably mounted on the ends of the table main unit 100, respectively. The pair of side walls 92 are provided with guide walls 104 (in FIG. 6, only one of them is shown) which are separated from the connecting wall 94 by a fixed distance. The rollers 102 are rotatably received between the sides of the connecting wall 94 and the pair of guide walls 104. A block member 106 which elongates so as to pass through the slot 96 of the connecting wall 94 is disposed on the center area of the first table main unit 100. Attaching members 110 and 118 are fixed to the ends in the vertical direction of the connecting wall 94. A screw shaft 112 is rotatably supported between the attaching members 110 and 118. The screw shaft 112 is screwed with the block member 106. One end portion of the screw shaft 112 is passed through the attaching member 118 so as to be downward projected. A Z-axis control motor 114 is drivingly coupled with the projected end portion. The Z-axis control motor 114 is fixed to the connecting wall 94 via the attaching member 118. According to this configuration, the rollers 102 are guided by the connecting wall 94 and the guide walls 104, and the rotation of the Z-axis control motor 114 causes the first moving table 98 to vertically move. Namely, the first moving table can be moved between the upper end position where the block member 106 is positioned at the upper end of the slot 96, and the lower end position where the block member 106 is positioned at the lower end of the slot 96.

Figure 6:
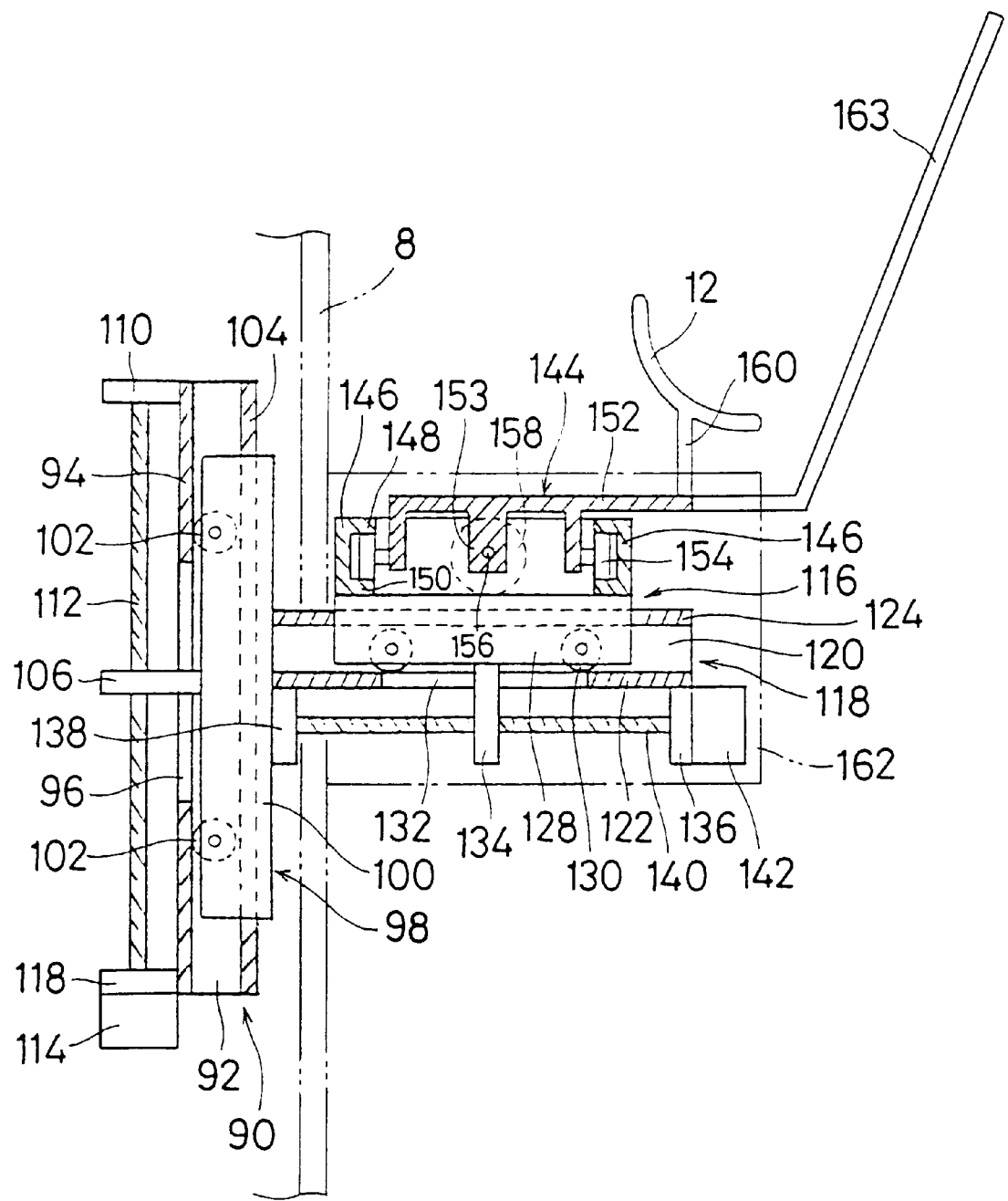
FIG. 6 is a section view showing a position adjusting mechanism in the X-ray imaging apparatus of FIG. 1.

A second moving table 116 is mounted on the first moving table 98 so as to be movable in the anteroposterior direction (in FIG. 6, the rightward and leftward direction). A guide frame 118 is fixed to the outer face of the first table main unit 100. The guide frame 118 has a pair of side walls 120 (in FIG. 6, only one of them is shown) which are arranged with being separated from each other in a lateral direction. A connecting wall 122 is disposed between the pair of side walls 120. A guide wall 124 is disposed on each of the side walls 120. The second moving table 116 is mounted between the pair of side walls 120 so as to be movable in the anteroposterior direction. The second moving table 116 comprises a second table main unit 128 which is rectangular. A pair of rollers 130 are rotatably mounted on the ends of the table main unit 128, respectively. The rollers 130 are rotatably received between the connecting wall 122 and the pair of guide walls 124. In the same manner as the first moving table 98, a block member 134 which elongates so as to pass through a slot 132 which is formed in the connecting wall 122 is disposed on the second table main unit 128. The block member 134 is screwed with a screw shaft 140 which is rotatably supported between attaching members 136 and 138 disposed on the connecting wall 122. One end portion of the screw shaft 140 is passed through the attaching member 136 so as to be forward projected. An X-axis control motor 142 is drivingly coupled with the projected end portion. The X-axis control motor 142 is fixed to the connecting wall 122 via the attaching member 136. According to this configuration, also in the second moving table 116, the rollers 130 are guided by the connecting wall 122 and the guide walls 124, thereby allowing the second table main unit 128 to be movable in the anteroposterior direction which are perpendicular to the first moving table 98. The second moving table can be moved between the forward end position where the block member 134 is positioned at the front end of the slot 132, and the rearward end position where the block member 134 is positioned at the rear end of the slot 132.

A third moving table 144 is mounted on the second moving table 116 so as to be movable in the lateral direction (the direction perpendicular to the sheet in FIG. 6). A pair of guide members 146 are fixed to the upper face of the second table main unit 128 with being separated from each other in the anteroposterior direction. Guide walls 148 and 150 are disposed on each of the guide members 146. The third moving table 144 is placed between the pair of guide members 146. The third moving table 144 comprises a third table main unit 152 which is rectangular. A pair of rollers 154 are rotatably mounted on the ends of the table main unit 152, respectively. The rollers 154 are rotatably received between the guide walls 148 and 150 of the pair of guide walls 146. A block member 153 is disposed on the third table main unit 152. A screw shaft 156 is rotatably supported between attaching members (not shown) which are disposed on the second table main unit 128. The block member 153 is screwed with the crew shaft 156, and a Y-axis control motor 158 is drivingly coupled with the crew shaft 156. According to this configuration, also in the third moving table 144, the rollers 154 are guided by the guide walls 148 and 150, thereby allowing the third table main unit 152 to be movable in a predetermined range in the lateral direction which is perpendicular to the moving direction of the second moving table 116.

The chin rest 12 has a support rod 160. The lower end of the support rod 160 is fixed to the third moving table 144. In the embodiment, as seen from FIGS. 1 and 6, the second and third moving tables 116 and 144 are covered by a protective cover 162 which is vertically moved integrally with the movement of the first moving table 98. A slot is formed in the protective cover 162. The support rod 160 is upward projected through the slot. In the embodiment, ear rods 163 are disposed on the third moving table 144. The tip ends of the ear rods 163 are to be respectively put on the ears of the patient of the object. This operation of putting the ear rods 163 on the ears enables the object to be more correctly held at the predetermined position.

In this configuration, when the Z-axis control motor 114 is rotated in a predetermined direction (or a direction opposite to the predetermined direction), the rotation of the screw shaft 112 causes the first table main unit 100 to be moved in the upward direction (or the downward direction) with respect to the elevator frame 8, i.e., the apparatus frame 2. When the X-axis control motor 142 is rotated in a predetermined direction (or a direction opposite to the predetermined direction), the rotation of the screw shaft 140 causes the second table main unit 128 to be moved in the forward direction (or the rearward direction) with respect to the elevator frame 8. When the Y-axis control motor 158 is rotated in a predetermined direction (or a direction opposite to the predetermined direction), the rotation of the screw shaft 156 causes the third table main unit 152 to be moved in the leftward direction (or the rightward direction). When the X-, Y-, and Z-axis control motors 142, 158, and 114 are controlled as required, therefore, the object placed on the chin rest 12 can be positioned at the predetermined position, or the predetermined imaging region between the X-ray source 28 and the image sensor 38. The operation of positioning the chin rest 12 will be described later in detail.

Figure 8:
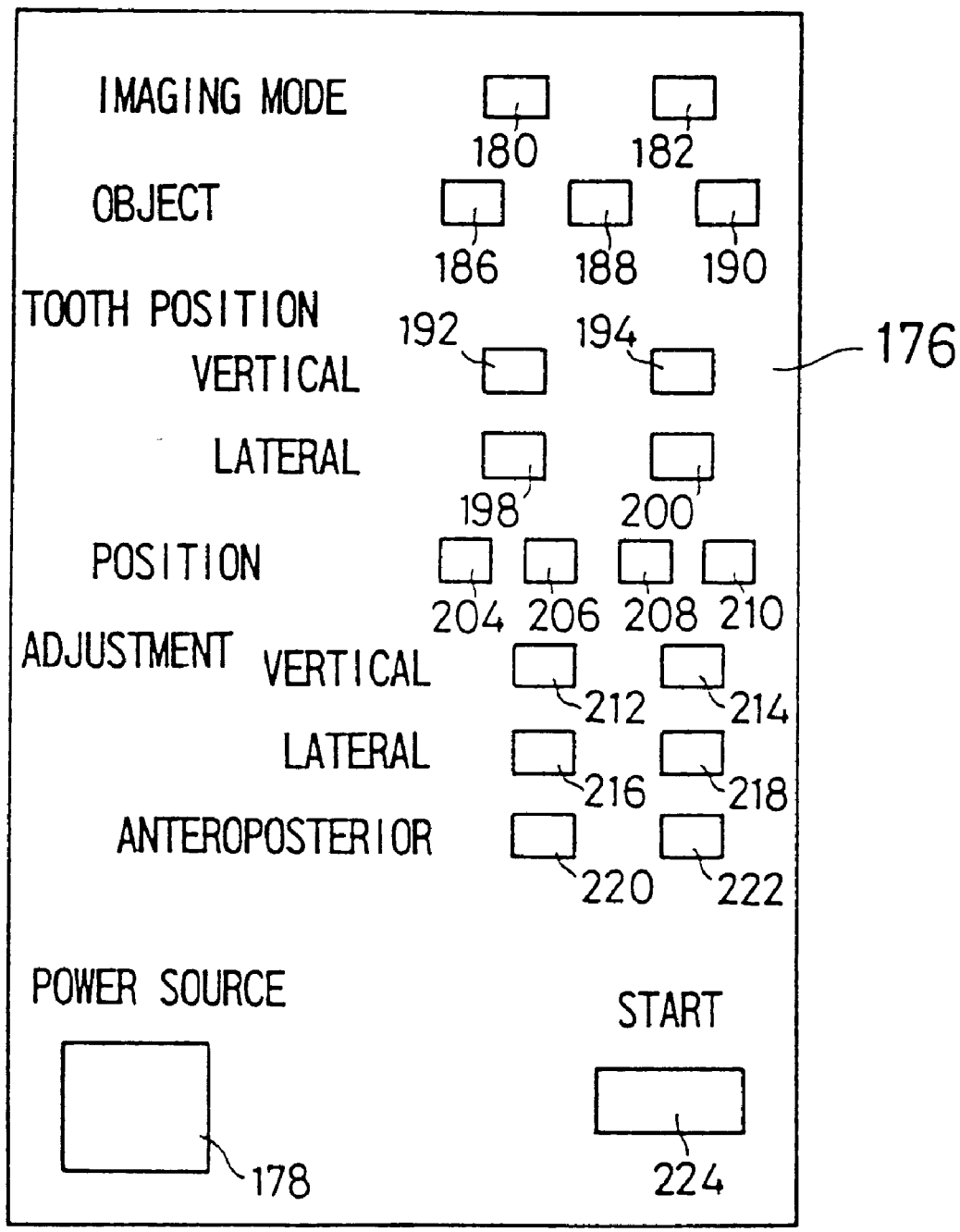
FIG. 8 is a front view showing an operation panel in the X-ray imaging apparatus of FIG. 1.

The motors 15, 42, 44, 46, 52, 54, 56, 58, 114, 142, 158 are configured by, for example, stepping motors and their operation are controlled by controlling means 170 of the X-ray imaging apparatus which is shown in FIG. 7. The controlling means 170 may be configured by, for example, a microprocessor, and controls the motors on the basis of a signal supplied from input means 174, as described later. In the embodiment, the input means 174 comprises an operation panel 176 which is shown in FIG. 8. A large switch 178 which is disposed in the left lower portion of the operation panel 176 is used for turning on and off the power source of the apparatus. When the switch is pressed one time, the X-ray imaging apparatus is powered on, and, when the switch is further pressed one time, the X-ray imaging apparatus is powered off. The operation panel 176 further has switches which are vertically arranged in the following sequence with starting from the upper side. Two switches 180 and 182 constitute the mode switching means for selecting the imaging mode. In the embodiment, either a CT mode or a panorama mode can be selected as the imaging mode. The switch 180 is a CT mode switch. When the switch 180 is pressed, the partial CT imaging is conducted as described later. The switch 182 is a panorama mode switch. When the switch 182 is pressed, the panoramic tomographic imaging is conducted as described later.

Object selection switches 186, 188, and 190 are arranged below the imaging mode changeover switches 180 and 182. The object selection switches 186, 188, and 190 are used in combination with tooth position selection switches 192 to 210 which are arranged below the object selection switches, in order to position the chin rest 12 at a position which corresponds to the imaging mode and also to the site to be imaged. The switch 186 is pressed in the case where the object is a young child, the switch 188 is pressed in the case where the object is an ordinary young child, and the switch 190 is pressed in the case where the object is an adult. The switches 192 and 194 are used for selecting the maxillary teeth or the mandibular teeth to be imaged. When the maxillary teeth are to be imaged, the switch 192 is pressed, and, when the mandibular teeth are to be imaged the switch 194 is pressed. The switches 198 and 200 are used for selecting the left teeth or the right teeth to be imaged. When the left teeth are to be imaged, the switch 198 is pressed, and, when the right teeth are to be imaged the switch 200 is pressed. The switches 204 to 210 are switches for specifying the position of the tooth to be imaged. When first and second teeth as counted with using the median line passing through the middle of the dental arch as the reference are to be imaged, the switch 204 is pressed. When third and fourth teeth are to be imaged, the switch 206 is pressed, when fifth and sixth teeth are to be imaged, the switch 208 is pressed, and, when seventh and eighth teeth are to be imaged, the switch 210 is pressed. The positioning of the chin rest 12 by using the switches 186 to 210 will be described later.

Switches 212 to 222 which are disposed below the switches 204 to 210 are used for finely adjusting the position of the chin rest 12. The switch 212 is a switch for upward moving the chin rest 12. During a period when the switch 212 is pressed, the Z-axis control motor 114 is rotated in the predetermined direction. The switch 214 is a switch for downward moving the chin rest 12. During a period when the switch 214 is pressed, the Z-axis control motor 114 is rotated in the direction opposite to the predetermined direction. The switch 216 is a switch for leftward moving the chin rest 12. During a period when the switch 216 is pressed, the Y-axis control motor 158 is rotated in the predetermined direction. The switch 218 is a switch for rightward moving the chin rest 12. During a period when the switch 218 is pressed, the Y-axis control motor 158 is rotated in the direction opposite to the predetermined direction. The switch 220 is a switch for forward moving the chin rest 12. During a period when the switch 220 is pressed, the X-axis control motor 142 is rotated in the predetermined direction. The switch 222 is a switch for rearward moving the chin rest 12. During a period when the switch 222 is pressed, the X-axis control motor 142 is rotated in the direction opposite to the predetermined direction.

An imaging start switch 224 is disposed below the switches 220 and 222. When the imaging start switch 224 is pressed, the X-ray irradiation to the object is started and the X-ray imaging is conducted.

The controlling means 170 has operation controlling means 172 for controlling operations of various motors, which operation controlling means 172 includes movement controlling means 173 for controlling operations of the X-axis control motor 42, the Y-axis control motor 44, and the rotation control motor 46 which constitute the moving means. As shown in FIG. 7, control signals from the operation controlling means 172 are supplied to the motors simultaneously and in time sequence. In the embodiment, the controlling means 170 further includes chin rest position storing means 226 which constitutes the position storing means, and process information storing means 228. The chin rest position storing means 226 stores object position information in each imaging mode, i.e., information relating to positional relationships among the X-ray source 28, the image sensor 38, and the site of the object to be imaged. The imaging position is determined in accordance with the imaging mode which is selected by the switches 180 and 182 which are disposed on the operation panel 176 (FIG. 8) and used for selecting the imaging mode. When the CT mode is selected, particularly, corresponding specific object position information is read out from object position information in the selected CT mode, on the basis of the size of the object which is selected by means of the switches 186 to 190 for selecting the object, and the imaging range and position which are designated by the switches 192 to 210 for designating the range and position of teeth to be imaged. On the basis of thus read out specific object position information, the operation controlling means 172 controls the X-, Y-, and Z-axis control motors 142, 158, and 114 as required, so that the chin rest 12 is positioned at the imaging position which is set by the operation panel 176. Therefore, the switches 186 to 210 constitute the position selecting means for setting the object position, and the chin rest 12 is automatically positioned at the position which is selected by the position selecting means. The set object position can be finely adjusted in vertical, lateral, and anteroposterior directions by pressing the switches 212 to 222 of the operation panel 176.

By contrast, when the panorama mode is selected, corresponding specific object position information is read out from object position information such as adult, child, or woman in the selected panorama mode, on the basis of the size of the object which is selected by means of the switches 186 to 190 for selecting the object. On the basis of thus read out specific object position information, the motors 114, 142, and 158 are controlled.

The process information storing means 228 stores CT process information for obtaining a partial CT image, and panorama process information for obtaining a panoramic tomographic image. When the switch 180 is pressed to select the CT mode, the CT process information of the process information storing means 228 is selected. The controlling means 170 controls operations of various components such as the motors on the basis of the CT process information. That is, during the partial CT imaging process, the movement controlling means 173 of the operation controlling means 172 controls the operation of the rotation control motor 46 on the basis of the CT process information so that the X-ray source 28 and the image sensor 38 are moved along a CT image formation locus. When the switch 182 is pressed to select the panorama mode, the panorama process information of the process information storing means 228 is selected. The controlling means 170 controls operations of various components such as the motors on the basis of the panorama process information. That is, during the panoramic imaging process, the movement controlling means 173 of the operation controlling means 172 simultaneously controls the operations of the X- and Y-axis control motors 42 and 44, and the rotation control motor 46 on the basis of the panorama process information so that the X-ray source 28 and the image sensor 38 are moved along a panoramic image formation locus. The CT image formation locus and the panoramic image formation locus will be described later.

In the embodiment, when the CT mode is selected, the primary and secondary slit means 30 and 40 define the primary and secondary CT slits 67a on the basis of the CT process information. When the CT mode is selected, the operation controlling means 172 controls the operations of the slit width control motors 52 and 54 and the slit height control motors 56 and 58 of the primary and secondary slit means 30 and 40 on the basis of the CT process information, so that the primary and secondary slit means 30 and 40 define the small square slits 67a shown in FIG. 5A, respectively. When the panorama mode is selected, the primary and secondary slit means 30 and 40 define the primary and secondary predetermined slits 67b on the basis of the panorama process information. When the panorama mode is selected, the operation controlling means 172 controls the operations of the slit width control motors 52 and 54 and the slit height control motors 56 and 58 of the primary and secondary slit means 30 and 40 on the basis of the panorama process information, so that the primary and secondary slit means 30 and 40 define the slender slits 67b shown in FIG. 5B, respectively.

Because of the above mentioned control, the slit width control motors 52 and 54 and the slit height control motors 56 and 58 of the primary and secondary slit means 30 and 40 constitute the primary- and secondary-slit switching means. The sizes of the slits 67 of the primary and secondary slit means 30 and 40 are controlled by the primary- and secondary-slit switching means.

Figure 9:
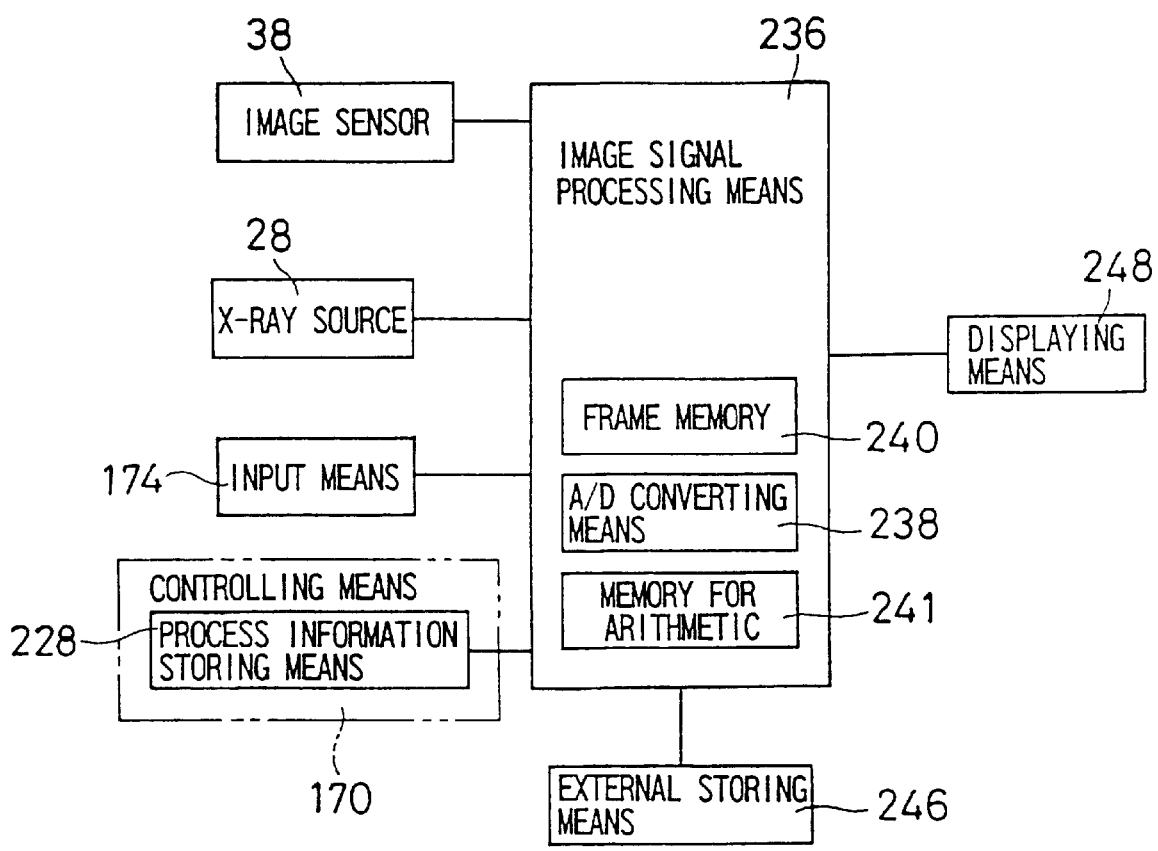
FIG. 9 is a block diagram showing an image signal processing system in the X-ray imaging apparatus of FIG. 1.

The image signal detected by the image sensor 38 is processed in the following manner. Referring to FIG. 9, the image signal output from the image sensor 38 is supplied to image signal processing means 236. The image signal processing means 236 may be configured by, for example, a microprocessor for image processing. The image signal processing means 236 in the embodiment comprises A/D converting means 238 for converting an analog signal into a digital signal, a frame memory 240 which stores image information, and a memory for arithmetic 241. The image signal supplied from the image sensor 38 to the image signal processing means 236 is converted into a digital signal by the A/D converting means 238, and digital-converted image information is stored in the frame memory 240. Plural sets of image information stored in the frame memory 240 are stored in the image memory for arithmetic 241. A predetermined arithmetic process corresponding to the selected imaging mode is conducted on image information read out from the image memory for arithmetic 241, thereby generating a tomographic image of the selected mode.

The above process will be described in more detail. The CT process information and the panorama process information stored in the process information storing means 228 of the controlling means 170 contain CT image process information and panoramic image process information, respectively. When the switch 180 (FIG. 8) is pressed to select the CT mode, the CT process information is selected from the process information storing means 228 and supplied to the image signal processing means 236. Then the image signal processing means 236 processes the image information stored in the frame memory 240 on the basis of the CT image process information contained in the CT process information, thereby generating a partial CT image. When the switch 182 (FIG. 8) is pressed to select the panorama mode, the panorama process information is selected from the process information storing means 228, and the image signal processing means 236 processes the image information stored in the frame memory 240 on the basis of the panoramic image process information contained in the panorama process information, thereby generating a panoramic tomographic image.

The signal of the tomographic image (the partial CT image or panoramic tomographic image) generated by the image signal processing means 236 is supplied to displaying means 248 which may be realized by, for example, a display device, and the tomographic image signal is displayed on the displaying means 248 as tomographic image information. As a result of the image processing, a tomographic image of the selected imaging mode is displayed on the displaying means 248. Furthermore, external storing means 246 for storing a tomographic image is disposed. As the external storing means 246, a hard disk apparatus or a magnetooptical disk apparatus may be used so that images are stored in a hard disk or a magnetooptical disk.

The embodiment is configured so that the exposure amount of X-rays emitted from the X-ray source 28 is adjusted on the basis of the density of the image information stored in the frame memory 240. The X-ray source 28 comprises an X-ray source (not shown). The X-ray exposure dose of the object can be adjusted by controlling the tube voltage, the cube current, the excitation period, and the like. As a result of the adjustment, a uniform tomographic image can be obtained.

As the image sensor 38, a MOS image sensor can be preferably used. Next, the operation principle of a MOS image sensor will be described with reference to FIG. 10.

Referring to FIG. 10A, a photodiode PD constituting a light receiving pixel converts entering light into an electric signal. A switch SW configured by a MOSFET is connected in series to the photodiode PD. The switch is connected also to the inverting terminal of an operational amplifier Q1. A feedback resistor R1 is connected to the operational amplifier Q1 so as to constitute a current/voltage converting circuit, whereby an input current is output as a voltage signal. A voltage V1 with respect to the ground (GND) is applied to the noninverting terminal of the operational amplifier Q1.

Referring to FIG. 10B, when a positive read pulse RD is supplied to the gate of the switch SW, the switch SW is opened and the photodiode PD is inversely biased so that the junction capacity C1 is charged by a predetermined amount of charges. The switch SW is then closed. When light enters during an accumulation period, the charges of the capacity are caused to be discharged by charges due to the light incidence, and hence the cathode potential of the photodiode PD gradually approaches the ground potential. The amount of the discharged charges is increased in proportion to the amount of the incident light. When the read pulse RD is then supplied to the gate of the switch SW and the switch SW is opened, charges corresponding to the charges which are discharged during the accumulation period are supplied via the feedback resistor R1 and the photodiode PD is returned to the inversely biased state so as to be initialized. At this time, a potential difference is produced across the feedback resistor R1 by the charging current. This potential difference is output from the operational amplifier Q1 as a voltage signal. The charging current corresponds to the discharge current due to the light incidence, and hence the amount of the incident light can be detected on the basis of the output voltage.

FIG. 11 is a section view showing the structure of the X-ray image sensor 38. Optical fiber elements (FOP) 254 through which an optical image is transmitted are disposed on a MOS image sensor 252 in which photodiodes PD constituting light receiving pixels are two-dimensionally arranged. A scintillator layer 256 which converts X-rays into visible light is formed on the optical fiber elements 254. The X-ray image having passed through the object is converted into a visible light image by the scintillator layer 256. The visible light image is transmitted by the optical fiber elements 254, and then subjected as it is to the photoelectric conversion by the MOS image sensor 252.

Figure 12:
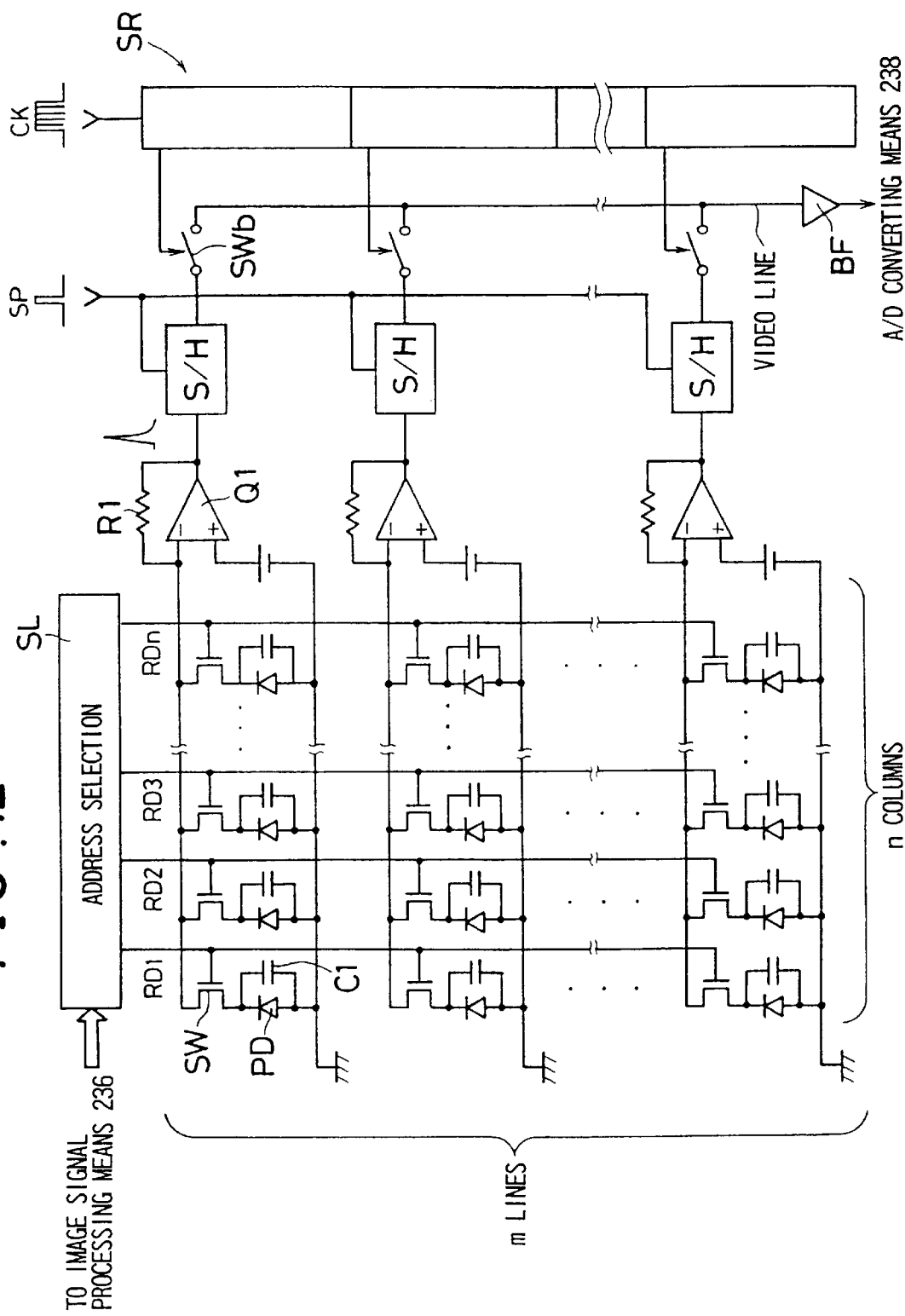
FIG. 12 is a circuit diagram showing a driving circuit for the MOS sensor in the X-ray imaging apparatus of FIG. 1.

FIG. 12 shows a driving circuit for the MOS image sensor 252. The photodiodes PD constituting light receiving pixels are arranged into a matrix of m lines×n columns. A junction capacity C1 is connected in parallel with each photodiode PD, and the read switch SW is connected in series to each photodiode PD. An address selection circuit SL is connected to the gates of the switches SW. The photodiode PD from which image information is to be read out is selected on the basis of a signal from the image signal processing means 236.

The outputs of the switches SW of each line are connected to each other and then supplied to corresponding one of operational amplifiers Q1 constituting the current/voltage converting circuit. The output of the operational amplifier Q1 is sampled by a sample and hold (S/H) circuit. Each sample and hold circuit is connected to a switch SWb which is closed and opened by an m-stage shift register SR. The switches SWb are sequentially closed and opened, so that the sampled signals are supplied as a time-series signal to the A/D converting means 238 of the image signal processing means 236. An integration circuit may be inserted between the operational amplifier Q1 and the sample and hold circuit S/H. The integration circuit integrates the current (or the voltage) and the sample and hold circuit S/H samples the integrated amount. The provision of the integration circuit causes the sampled amount to contain an integration time. As a result, the sensitivity of the detection signal can be enhanced.

Figure 13:
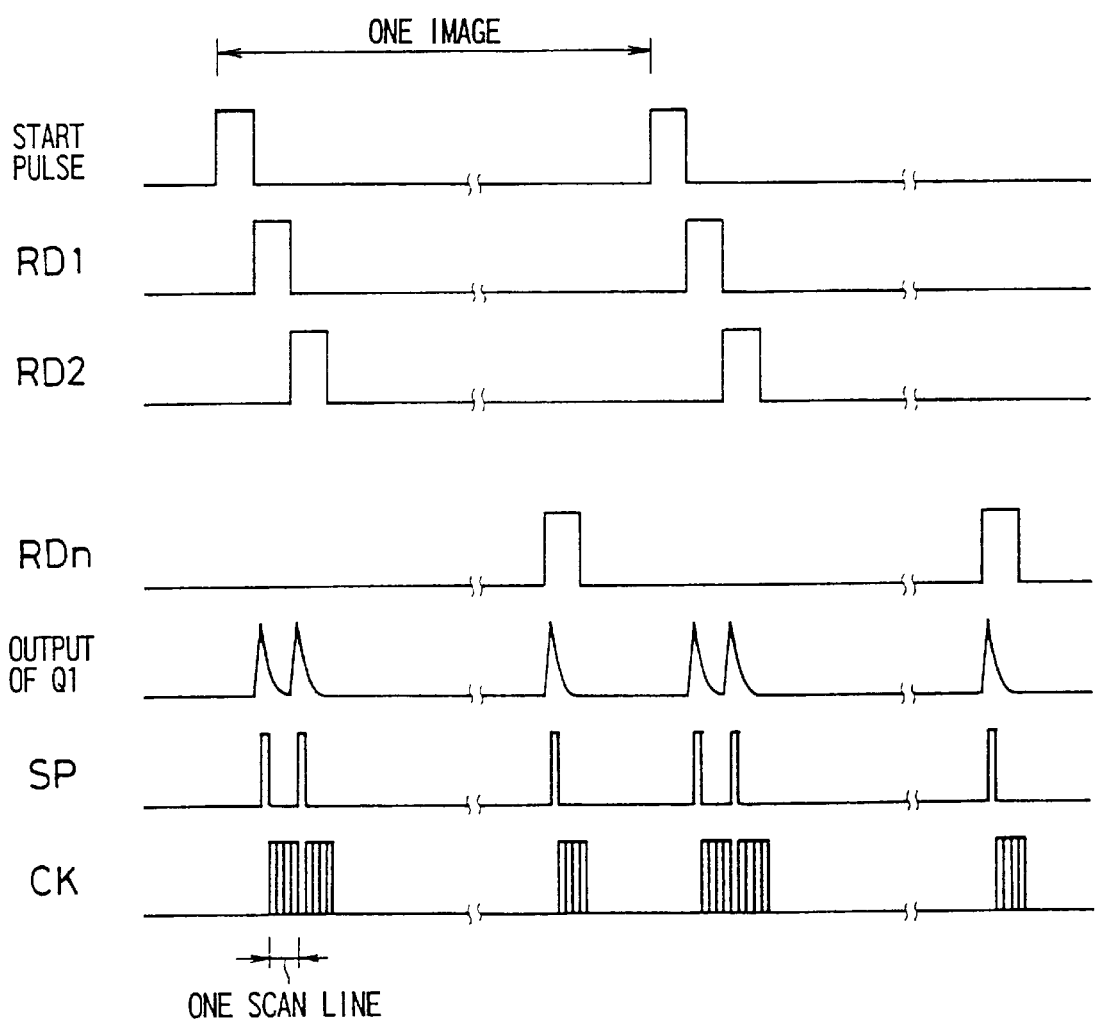
FIG. 13 is a timing chart illustrating the operation of the MOS sensor driving circuit of FIG. 12.

FIG. 13 is a timing chart illustrating the operation of the driving circuit of FIG. 12. Hereinafter, an example in which a shift register is used as the address selection circuit SL will be described. The address selection circuit SL is activated by a start pulse supplied from the image signal processing means 236, and outputs in sequence a first-column read pulse RD1, a second-column read pulse RD2, . . . , an nth-column read pulse RDn in synchronization with a read clock supplied from the image signal processing means 236.

When the first-column read pulse RD1 is supplied to the gates of the switches SW of the first column, for example, charges corresponding to the amount of the incident light of the photodiodes PD of the first column are read out, and the operational amplifiers Q1 output voltage signals. A sampling pulse SP is supplied to the sample and hold circuits so as to sample the timing when output of the operational amplifier Q1 reaches its peak value. The sampled signals are supplied from the shift register SR, and transferred by a shift clock signal CK consisting of m pulses until the next sampling pulse SP is supplied, so as to be output as an image signal for one scan line. Also for the second and subsequent columns, in the same manner as described above, signals for m lines are read out in parallel by one read pulse and a time series signal for one scan line is configured by the shift register SR.

Figure 14:
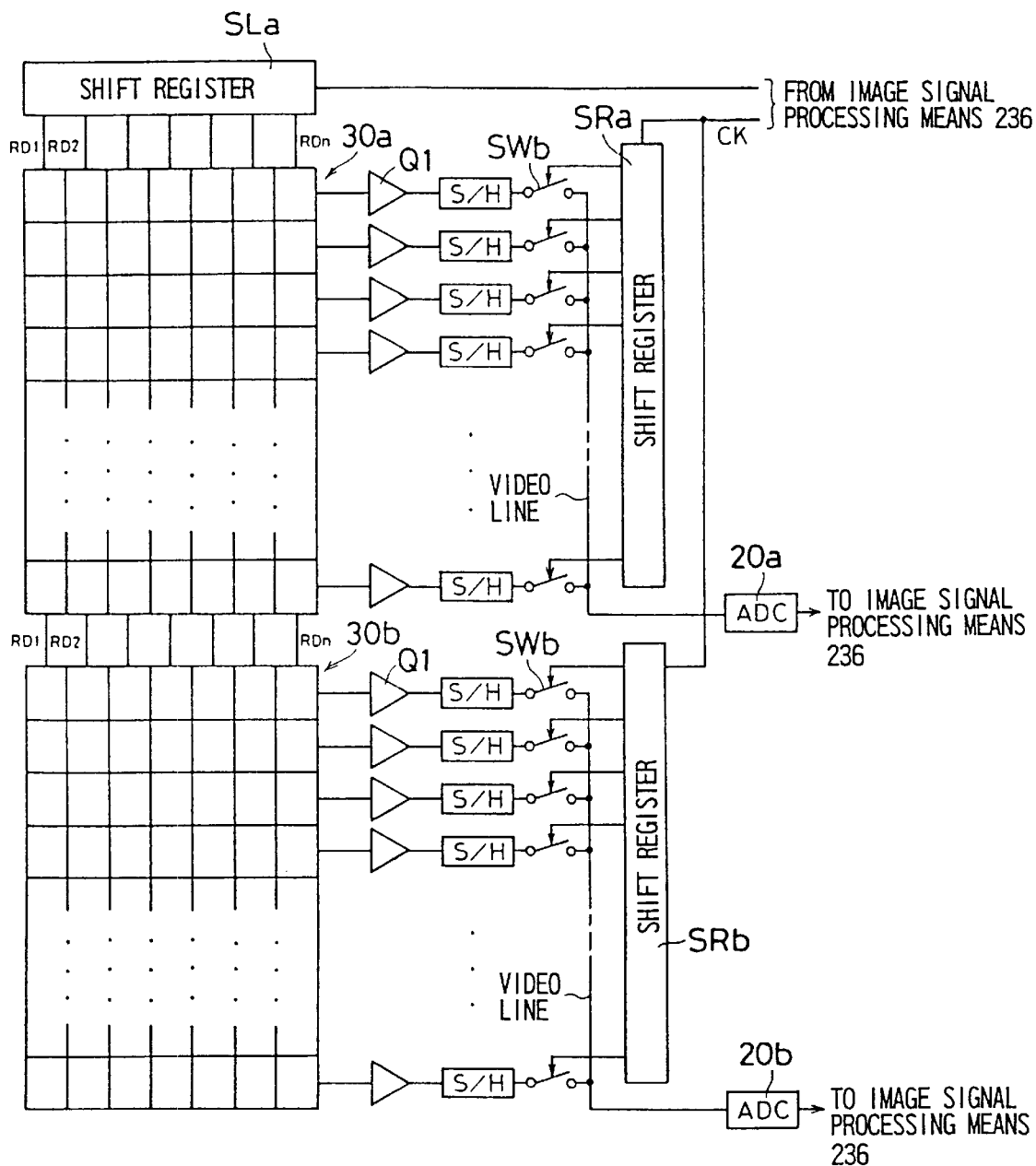
FIG. 14 is a diagram of a circuit in which MOS sensors are connected in two stages.

FIG. 14 shows an example of a circuit in which MOS image sensors are connected in plural stages. Two MOS image sensors 252a and 252b having light receiving pixels of m lines and n columns are aligned in the column direction, and connected so that read pulses RD1 to RDn from a shift register SLa serving as the address selection circuit SL are driven in the same column. In response to a single read pulse, signals are read out in parallel from 2m photodiodes and then supplied to 2m operational amplifiers Q1 and 2m sample and hold circuits which correspond to the columns, respectively. Two shift registers SRa and SRb are disposed so as to correspond to the MOS image sensors 252a and 252b. The outputs of the sample and hold circuits are transferred as time series signals to the image signal processing means 236 by sequentially closing and opening 2m switches SWb. The signals supplied to the image signal processing means 236 are converted into digital signals by the A/D converting means 238 and then stored in the frame memory 240. In FIG. 14, the example which uses two MOS image sensors 252a and 252b is shown. Alternatively, MOS image sensors may be connected in three or more stages.

Next, referring mainly to FIGS. 2, 7, 9, and 15 to 17, the imaging operation of the X-ray imaging apparatus will be described.

Figure 15:
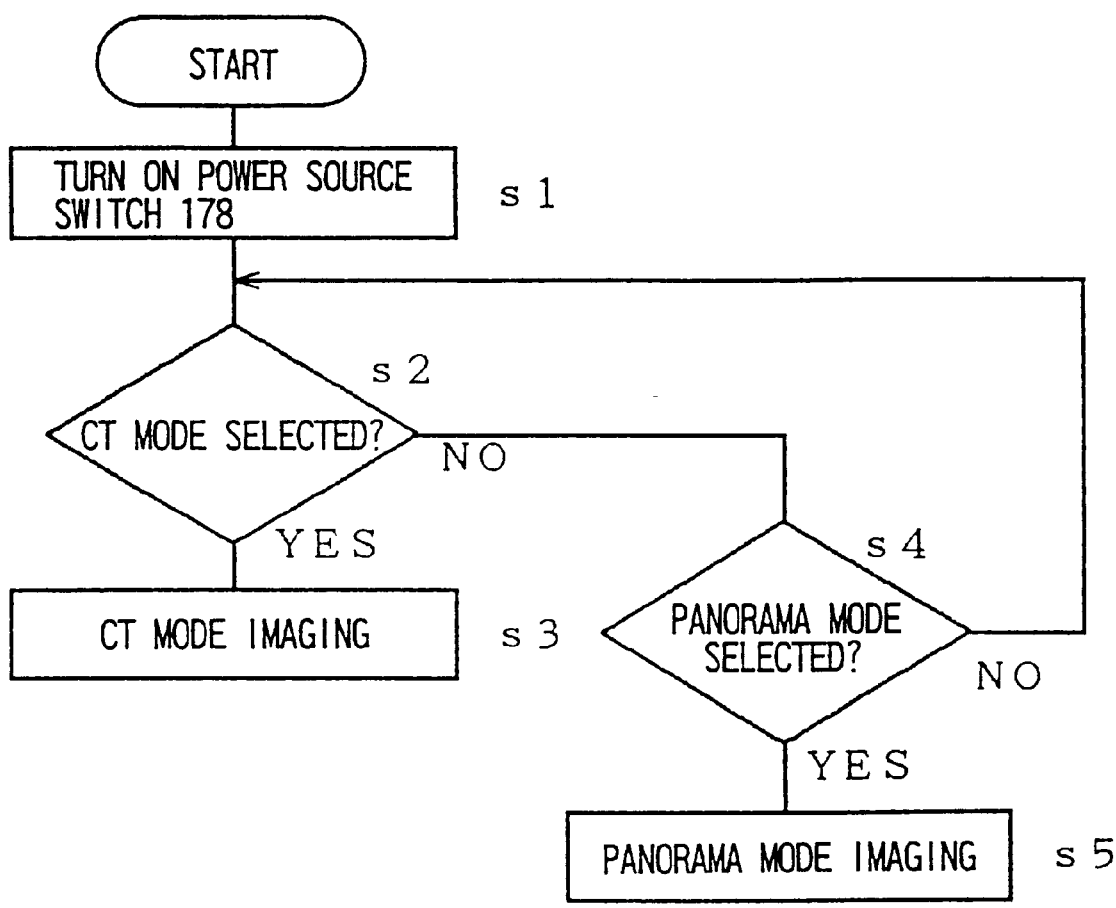
FIG. 15 is a flowchart illustrating an operation of switching over the imaging mode in the X-ray imaging apparatus of FIG. 1.

Referring to FIG. 15, first, a flowchart relating to the selection of the imaging mode will be described. When the power source switch 178 (FIG. 8) of the operation panel 176 is closed (turned on), the control proceeds to step S1 and a current is supplied to the X-ray imaging apparatus, whereby the X-ray imaging which will be described later is enabled.

Next, it is judged in step S2 whether the CT mode is set or not. If the switch 180 (FIG. 8) of the operation panel 176 is pressed to select the CT mode, the control proceeds from step S2 to step S3 in which the CT mode imaging operation is executed. If the switch 180 is not pressed, the control proceeds to step S4, and it is judged whether the switch 182 (FIG. 8) is pressed or not. If the switch 182 is pressed to select the panorama mode, the control proceeds from step S4 to step S5 in which the panorama mode imaging operation is executed. If the switch 182 is not pressed, the control returns to step S2, and the above-mentioned routine is repeatedly executed until one of the switches 180 and 182 is pressed.

Figure 16:
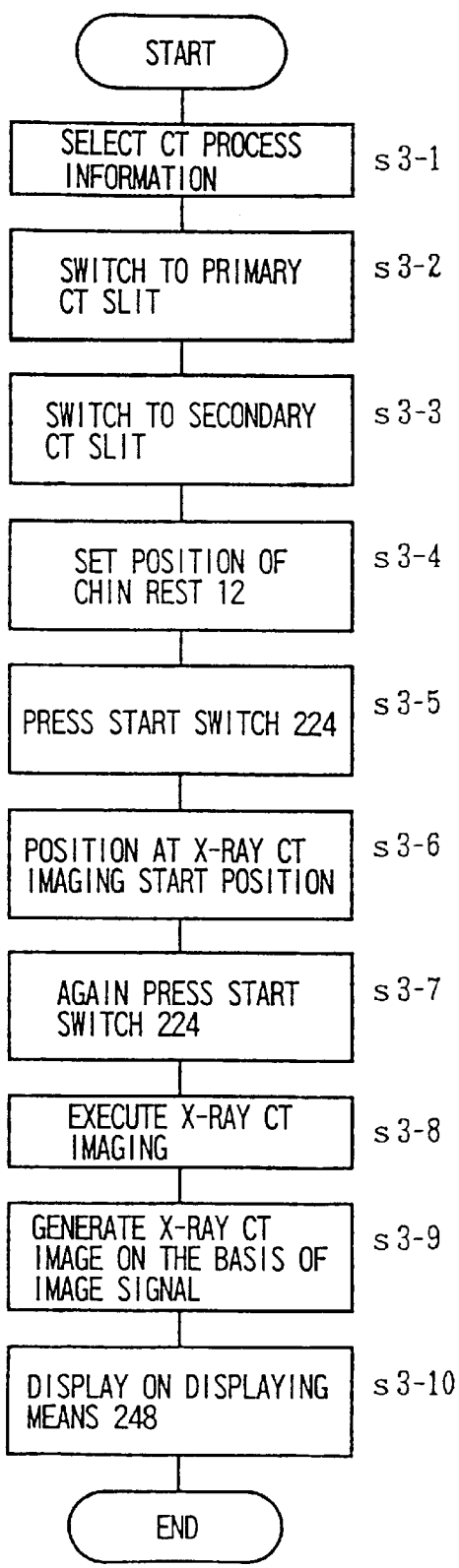
FIG. 16 is a flowchart illustrating an imaging operation in the case where a CT mode is selected.

The CT mode imaging operation which is executed in step S3 in the case where the CT mode is selected in step S2 is conducted in accordance with a flowchart of FIG. 16. Referring to FIGS. 7 to 9, and 16, if the CT mode is selected, process information corresponding to the selected imaging mode, i.e., the CT process information is selected in step S3-1 from the process information storing means 228 of the controlling means 170. Next, in step S3-2, the slit opening of the primary slit means 30 is set to the primary CT slit 67a (FIG. 5A) on the basis of the selected CT process information. Then, in step S3-3, the slit opening of the secondary slit means 40 is set to the secondary CT slit 67a (FIG. 5A) on the basis of the CT process information. As described above, the operations of switching the slit openings in steps S3-2 and S3-3 are conducted by controlling the operations of the slit width control motors 52 and 54 and the slit height control motors 56 and 58 of the primary and secondary slit means 30 and 40 on the basis of the CT process information. When the primary and secondary slit means 30 and 40 are set to the primary and secondary CT slits 67a in this way, the X-ray imaging apparatus enters the state where the partial CT imaging is enabled. Steps S3-2 and S3-3 are not required to be executed in the order described above, and may be executed in a reversed order.

Thereafter, the chin rest 12 is positioned at the predetermined position. As described above, the positioning of the chin rest 12 is conducted by pressing the switches 186 to 210 of the operation panel 176, and by, if necessary, further pressing the switches 212 to 222. When the switches 186 to 210 are pressed to input information relating to the size of the object and the imaging site of the partial CT imaging, position information corresponding to the input information is read out from the object position information stored in the chin rest position storing means 226 of the controlling means 170. The chin rest 12 is positioned on the basis of the read out position information. As described above, the positioning is conducted by controlling the operations of the X-, Y-, and Z-axis control motors 142, 158, and 114 of the object position adjusting mechanism 10 on the basis of the position information read out from the object position information.

When the chin rest 12 is positioned at the imaging position in this way, the site to be imaged of the object is positioned in an imaging region 262 (FIG. 18) in a state where the chin is placed on the chin rest 12.

Next, a start switch 224 is pressed in step S3-6 so that the supporting means 18, i.e., the support arm 24 is positioned at a specific angular position which elongates in the lateral direction, so that the X-ray source 28 and the image sensor 38 are positioned at respective partial X-ray CT imaging start positions (step S3-6). The positioning of the supporting means 18 is conducted by controlling the operation of the rotation control motor 46 by the operation controlling means 172 on the basis of the CT process information.

The specific angular position which laterally elongates means a specific angular position where a line Q connecting the X-ray source 28 and the image sensor 38 makes an angle within an angle range θ of ±30 deg. with respect to a just lateral direction. In the embodiment, the components are positioned at the angular position shown in FIG. 20 where the line Q elongates in a just lateral direction.

Thereafter, the patient of the object stands on the base 4, the chin is positioned on the chin rest 12, and the ear rods 163 are put on the ears of the patient. This positioning allows the site to be imaged (for example, an imaging site of the patient), to be placed in the imaging region 262 (indicated by a circle in FIG. 18) which is between the X-ray source 28 (FIG. 2) and the image sensor 38 (FIG. 2). Therefore, an excellent tomographic image can be obtained without conducting a cumbersome positioning operation.

Figure 20:
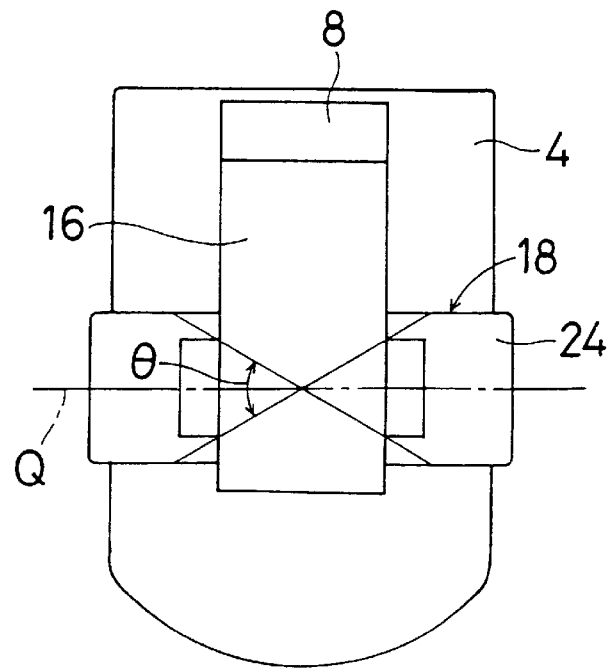
FIG. 20 is a plan view showing the X-ray imaging apparatus of FIG. 1 in a condition that supporting means is at a specific angler position.

In the embodiment, as seen from FIG. 20, the patient passes through between the first attaching portion 26 and the second attaching portion 32 of the support arm 24 to move toward the imaging region 262 from the forward direction. Therefore, the access route for the patient to the imaging region 262 elongates between the first and second attaching portions 26 and 32 of the support arm 24 in the anteroposterior direction (vertical direction in FIG. 20). In the thus configured X-ray imaging apparatus, by positioning the supporting means 18 at the specific angler position shown in FIG. 20, for example, the first attaching portion 26 (the X-ray source 28, and the like which are attached to the unit) is positioned on the left side of the access route in FIG. 20, and the second attaching portion 32 (the image sensor 38, and the like which are attached to the unit) is positioned on the right side of the access route in FIG. 20. As a result, the first and second attaching portions 26 and 32 escape from the access route for the patient, and hence the patient can easily enter the imaging region 262. Alternatively, the apparatus may be configured so that, at the specific angular position, the first attaching portion 26 is positioned on the right side of the access route, and the second attaching portion 32 is positioned on the left side of the access route.

In the procedure described above, the chin rest 12 is first positioned at the imaging position, the X-ray source 28 and the image sensor 38 are respectively positioned at the imaging start positions, and the patient then moves to the imaging region 262. This order may be suitably changed. For example, the patient may be first introduced to the imaging position, the chin rest 12 may be positioned at the imaging position with the chin being placed thereon, and the X-ray source 28 and the image sensor 38 may be then respectively positioned at the imaging start positions.

Figure 18:
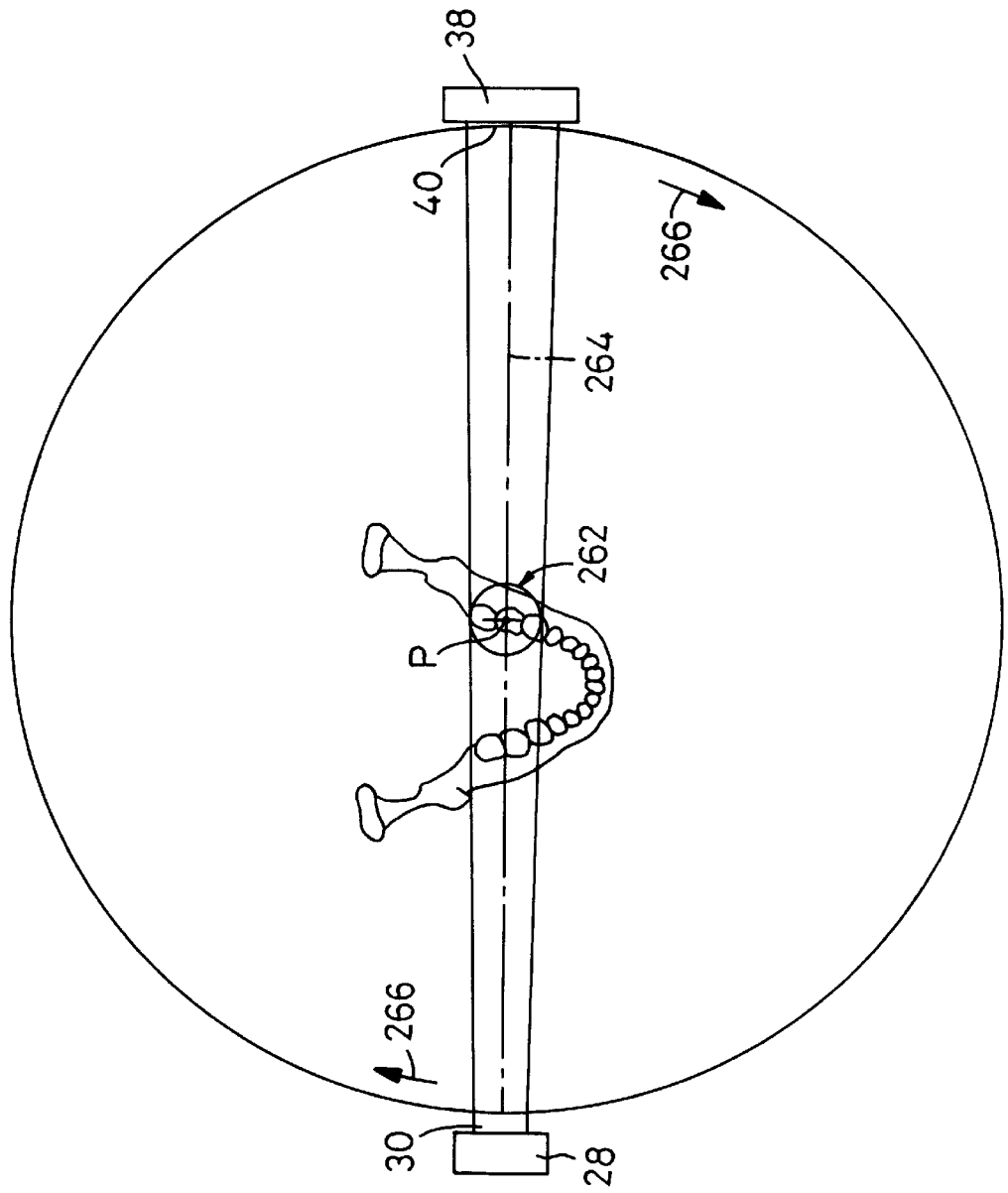
FIG. 18 is a simplified diagram illustrating movement loci of an X-ray source and an image sensor in the case where the CT mode is selected.

After the positioning of the object with respect to the X-ray imaging apparatus is completed, the start switch 224 of the operation panel 176 is again pressed. Then, the operation proceeds from step S3-7 of FIG. 16 to step S3-8 and the partial X-ray CT imaging is executed. The imaging region 262 is irradiated with X-rays emitted from the X-ray source 28. X-rays which have passed through the object are detected by the image sensor 38. During the X-ray irradiation, the X-ray source 28 and the primary slit means 30, and the image sensor 38 and the secondary slit means 40 are moved along the CT image formation locus, that is, the supporting means 18 supporting these components is rotated about the rotation axis. More specifically, in the partial CT imaging, a range of, for example, about 50 mm, i.e., a local region containing two or three teeth which range centered at the middle point P (the middle point P coincides with the center axis of the rotation shaft 22) of a line 264 connecting the X-ray source 28 and the image sensor 38 as shown in FIG. 18 is used as the imaging region 262. During the partial CT imaging process, the middle point P is not varied. The X-ray source 28 and the image sensor 38 are revolved at a constant rotational speed about the middle point P by 360 deg. in, for example, a clockwise direction indicated by an arrows 266. As a result of the revolution, an omnidirectional or 360-deg. image of the site to be imaged which is positioned in the imaging region 262 is obtained. Since X-rays emitted from the X-ray source 28 pass through the primary slit means 30, X-rays impinges on the imaging region, in the form of a quadrangular pyramid. Therefore, the imaging region 262 is always formed into a columnar shape of, for example, a diameter of 50 mm and a height of about 50 mm. The imaging region 262 is positioned on an extension line of the rotation axis of the rotation shaft 22. An image signal obtained by the image sensor 38 is converted into a digital signal by the A/D converting means 238 and then stored in the frame memory 240. In the embodiment, since the primary slit means 30 defines the square primary CT slit 67a, X-rays from the X-ray source 28 impinges on the imaging region 262, in the form of a quadrangular pyramid. The image sensor 38 generates a signal of the corresponding image at intervals of one deg. in the revolution direction indicated by the arrows 266, so that signals corresponding to 360 images are generated as a result of the revolution of 360 deg. These image signals are stored in the frame memory 240. Since the X-ray source 28 and the image sensor 38 are moved as described above, the CT locus information is that the X-ray source 28 and the image sensor 38 are revolved about the invariable middle point P. In the case of the CT mode, the operation of the rotation control motor 46 is controlled during the partial CT imaging process on the basis of the CT process information, and the support arm 24 is rotated in the direction indicated by the arrows 266.

When the partial X-ray CT imaging in step S3-8 is ended, the operation proceeds to step S3-9, and a partial CT image is generated on the basis of the obtained images. When a partial CT image is to be generated, information of the images stored in the frame memory 240 is read out, and the read out image information is stored in a memory for arithmetic 241. The image signal processing means 236 conducts an image processing on the images read out from the memory for arithmetic 241 on the basis of the CT image process information. As a result of the image processing, a partial CT image is obtained.

The generated partial CT image is displayed in step S3-10 on the displaying means 248. In this way, a partial CT image of the predetermined site of the object is obtained. For example, an implant operation in the dental treatment can be easily performed while observing the partial CT image displayed on the displaying means 248.

After the partial CT imaging process, the support arm 24 is again positioned at the specific angular position shown in FIG. 20. Since the support arm 24 is positioned in this way also after the imaging process is ended, the patient of the object can forward move from the imaging region 262 so as to go out of the imaging region 262. At the specific angular position, the line Q connecting the X-ray source 28 and the image sensor 38 exists within the angle range θ of ±30 deg. with respect to a just lateral direction, and hence the patient can easily enter or exit from the imaging region 262 (FIG. 20).

Figure 17:
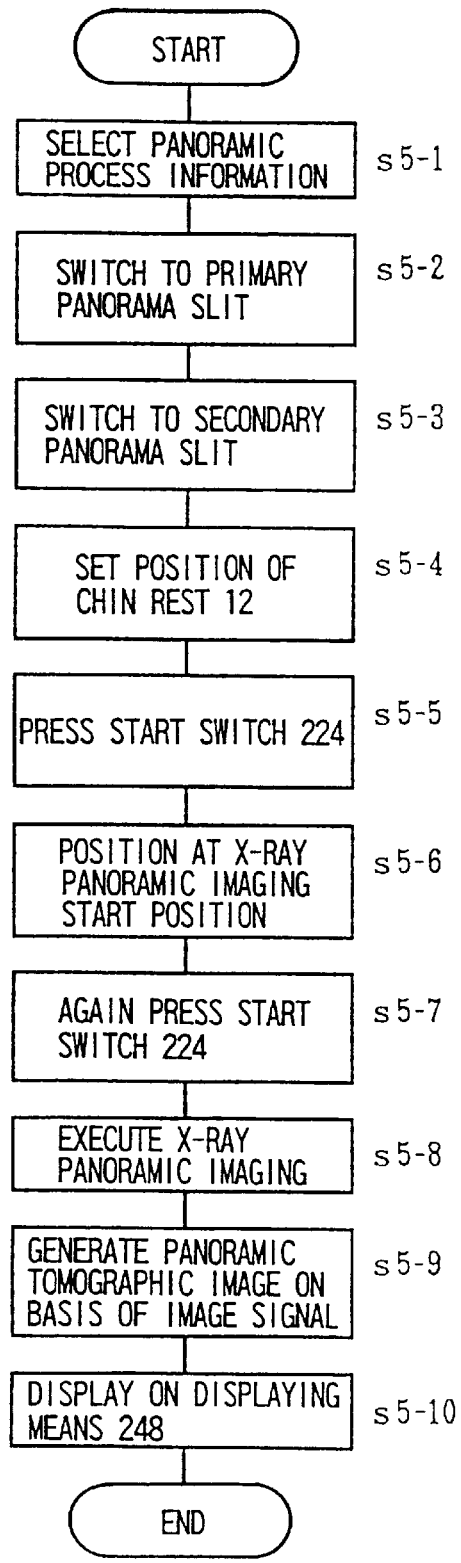
FIG. 17 is a flowchart illustrating an imaging operation in the case where a panorama mode is selected.

The panoramic imaging operation which is executed in step S5 in the case where the panorama mode is selected in step S4 is conducted in accordance with the flowchart of FIG. 17. Referring to FIGS. 7 to 9, and 17, if the panorama mode is selected, process information corresponding to the selected imaging mode, i.e., the panorama process information is selected in step S5-1 from the process information storing means 228. Next, in step S5-2, the slit opening of the primary slit means 30 is set to the primary panorama slit 67b (FIG. 5B) on the basis of the selected panorama process information. In step S5-3, the slit opening of the secondary slit means 40 is set to the secondary panorama slit 67b (FIG. 5B) on the basis of the panorama process information. As described above, the operations of switching the slit openings in steps S5-2 and S5-3 are conducted by controlling the operations of the slit width control motors 52 and 54 and the slit height control motors 56 and 58 of the primary and secondary slit means 30 and 40 on the basis of the panorama process information. When the primary and secondary slit means 30 and 40 are set to the primary and secondary panorama slits 67b in this way, the X-ray imaging apparatus enters the state where the panoramic imaging is enabled. Steps S5-2 and S5-3 may be executed in a reversed order.

Thereafter, the chin rest 12 is positioned at the predetermined position. The positioning is conducted by controlling the operations of the X-, Y-, and Z-axis control motors 142, 158, and 114 of the object position adjusting mechanism 10 (step S5-4).

Next, the start switch 224 is pressed in step S5-5 so that the supporting means 18 is positioned at a predetermined position and at a predetermined angular position (for example, an angular position at which the rotation axis of the support arm 24 is positioned at one end of an envelope 268 (FIG. 19) and X-rays from the X-ray source 28 to the image sensor 38 impinge on the dental arch 272 (FIG. 19) at a substantially perpendicular angle), so that the X-ray source 28 and the image sensor 38 are positioned at respective X-ray panoramic imaging start positions (step S5-7). The positioning of the supporting means 18 is conducted by controlling the operations of the X- and Y-axis control motors 42 and 44, and the rotation control motor 46 of the plane moving mechanism 20 by the movement controlling means 173 on the basis of the panorama process information.

Thereafter, the patient of the object is moved onto the base 4 and the chin is positioned on the chin rest 12, and the ear rods 163 are put on the ears of the patient. This positioning allows the site to be imaged (for example, an affected area), to be positioned at the predetermined position which is between the X-ray source 28 (FIG. 2) and the image sensor 38 (FIG. 2). Therefore, an excellent panoramic tomographic image can be obtained without conducting a cumbersome positioning operation.

Also in the X-ray panoramic imaging, the chin rest 12 is first positioned at the imaging position, the X-ray source 28 and the image sensor 38 are respectively positioned at the imaging start positions, and the patient then is introduced. The procedure may be changed so that, for example, the patient is first introduced onto the base 4, the chin is positioned at the imaging position while the chin is placed on the chin rest 12, and the X-ray source 28 and the image sensor 38 are then respectively positioned at the imaging start positions. Also, the procedure may be changed so that the support arm 24 is first positioned in the specific angler position described above (FIG. 20), the patient is introduced onto the base 4 under the condition that the support arm 24 is positioned in the specific angler position, and then the X-ray source 28 and the image sensor 38 are positioned at the imaging start positions.

Figure 19:
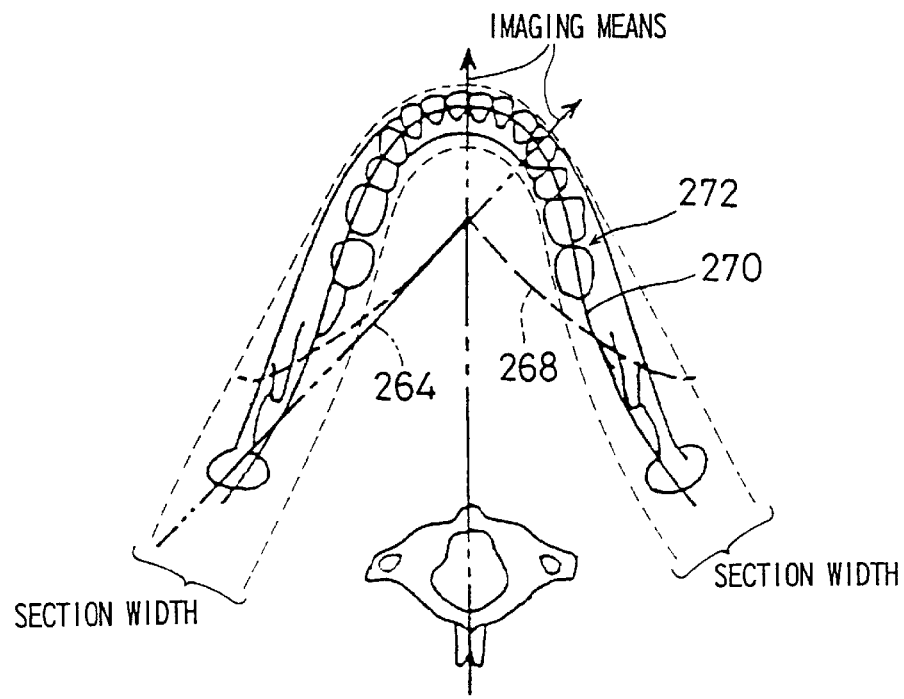
FIG. 19 is a simplified diagram illustrating a movement locus of the middle between the X-ray source and the image sensor and an image sensor in the case where the panorama mode is selected.

After the positioning of the object with respect to the X-ray imaging apparatus is completed, the start switch 224 of the operation panel 176 is again pressed. The operation of pressing the switch 224 causes the operation to proceed from step S5-7 to step S5-8 and the X-ray panoramic imaging is executed. The object is irradiated with X-rays emitted from the X-ray source 28. X-rays which have passed through the object are detected by the image sensor 38. During the X-ray irradiation, the X-ray source 28 and the primary slit means 30, and the image sensor 38 and the secondary slit means 40 are moved along the panoramic image formation locus. More specifically, in the panoramic tomographic imaging process, as shown in FIG. 19, the locus of the middle point (the middle point coincides with the center axis of the rotation shaft 22) of the line 264 which connects the X-ray source 28 and the image sensor 38 and which indicates the X-ray irradiation direction is moved along the curve (i.e., envelope) 268 indicated by the broken line. In FIG. 19, the line 270 indicated by the solid line shows the tomographic plane of the dental arch 272. In the panoramic imaging, X-rays emitted from the X-ray source 28 are directed in a direction which is substantially perpendicular to the tomographic plane 270. When the panoramic tomographic imaging is to be conducted along the dental arch 272, therefore, the support arm 24 is moved in a plane and rotated about the rotation shaft 22 as required. During the panoramic imaging process, the position of the rotation shaft 22 is changed every moment in this way. The positional change is realized by momentarily moving the rotation shaft 22 by the plane moving mechanism 20. In the embodiment, since the primary slit means 30 defines the slender square primary panorama slit 67b, X-rays from the X-ray source 28 impinge in the form of a slender quadrangular pyramid. Since the rotation axis of the rotation shaft 22 is moved and the support arm 24 is rotated about the rotation shaft 22 in this way, the panoramic locus information is that a combination of the above-mentioned movement of the rotation axis of the rotation shaft 22 and the rotation of the support arm 24 about the rotation axis causes the X-ray source 28 (including the primary slit means 30) and the image sensor 38 (including the secondary slit means 40) to be moved. In the X-ray panoramic imaging, usually, the rotation of the support arm 24 in the case where the molar tooth region is to be imaged is faster than that in the case where the anterior tooth region is to be imaged. In the case of the panorama mode, the operations of the X- and Y-axis control motors 42 and 44, and the rotation control motor 46 are simultaneously controlled during the panoramic imaging process on the basis of the panoramic locus information, so that the support arm 24 is moved and rotated as described above.

When the X-ray panoramic imaging in step S5-8 is ended, the operation proceeds to step S5-9 as shown in FIG. 17, and a panoramic tomographic image is generated on the basis of the obtained images. When a panoramic tomographic image is to be generated, information of the images stored in the frame memory 240 is read out, and the read out image information is stored in the memory for arithmetic 241. The image signal processing means 236 conducts an image processing on the images read out from the memory for arithmetic 241 on the basis of the panoramic image process information contained in the panorama process information. As a result of the image processing, a panoramic tomographic image is obtained.

In the same manner as a CT image, the generated panoramic tomographic image is displayed in step S5-10 on the displaying means 248. In this way, a panoramic tomographic image of the predetermined site of the object is obtained. The panoramic tomographic image displayed on the displaying means 248 can be used as information for a dental treatment or the like.

As seen from the above description, a tomographic image corresponding to the selected imaging mode, i.e., a tomographic image which is arbitrarily selected from a CT image and a panoramic tomographic image can be obtained from the single X-ray imaging apparatus.

It is preferable that after completion of the X-ray panoramic imaging, the support arm 24 is positioned at the specific angular position with respect to the horizontal arm 16 as shown in FIG. 20. Owing to such constitution the patient can easily go out of the imaging region.

Figure 21:
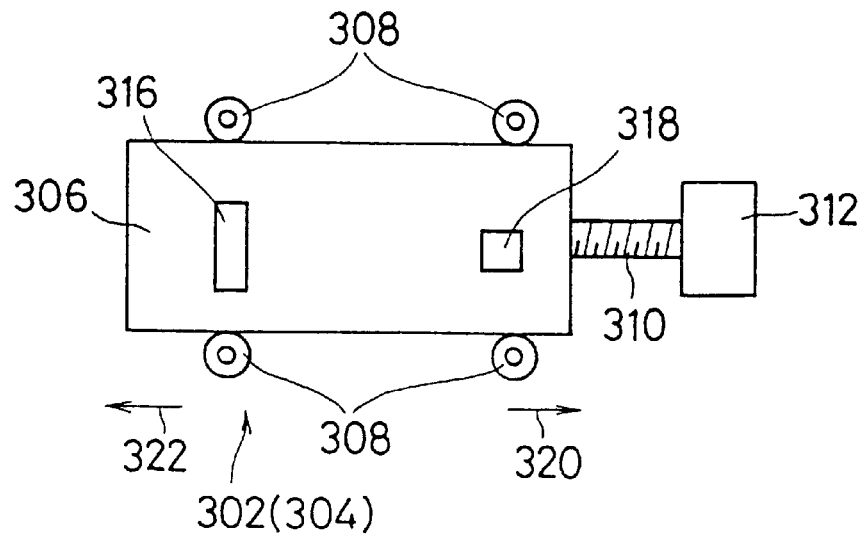
FIG. 21 is a front view showing a modification of the primary (secondary) slit means.

In the embodiment, the primary and secondary slit means 30 and 40 comprise the pair of width shield members 60 and 62 and the pair of height shield members 64 and 66, and the slit openings are adjusted by moving the width shield members 60 and 62 and the height shield members 64 and 66. Alternatively, the apparatus may be configured in the manner shown in FIG. 21 or 22. Referring to FIG. 21 showing a modification of the primary (secondary) slit means, illustrated primary (or secondary) slit means 302 (or 304) comprises a rectangular shield plate 306. The shield plate 306 is supported by four support rollers 308 so as to be movable in the right and left directions in FIG. 21. A driving screw shaft 310 is screwed with the shield plate 306. One end portion of the driving screw shaft 310 is drivingly coupled with a slit control motor 312. In the shield plate 306, formed are two slits which are separated from each other in the moving direction (the rightward and leftward direction in FIG. 21), i.e., a primary (or secondary) panorama slit 316 which is in the left portion of FIG. 21 and a primary (or secondary) CT slit 318 which is in the right portion. According to this configuration, the slit opening of the primary (or secondary) slit means 302 (or 304) can be switched by rotating the slit control motor 312 so as to move the shield plate 306 in the rightward direction indicated by an arrow 320 or the leftward direction indicated by an arrow 322. As understood from the above description, when the panorama mode is selected, the primary (or secondary) panorama slit 316 is positioned in front of the X-ray source 28 (or the image sensor 38), and, when the CT mode is selected, the primary (or secondary) CT slit 318 is positioned in front of the X-ray source 28 (or the image sensor 38). Also in the case where the thus configured primary (or secondary) slit means 302 (or 304) is used, the size of the slit opening can be automatically switched to the one corresponding to the selected imaging mode in the same manner as described above.

Figure 22:
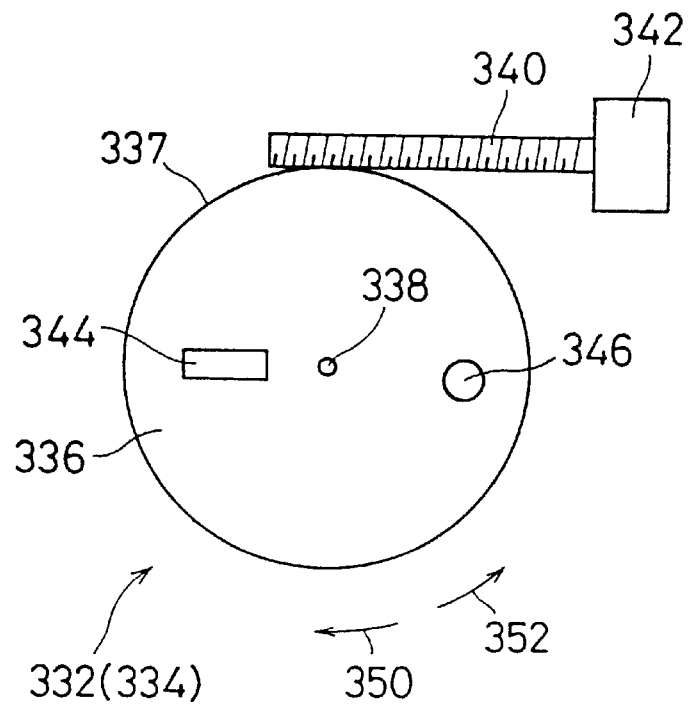
FIG. 22 is a front view showing another modification of the primary (secondary) slit means.

FIG. 22 shows another modification of the primary (secondary) slit means. Referring to FIG. 22, illustrated primary (or secondary) slit means 332 (or 334) comprises a circular shield plate 336. The shield plate 336 is provided with a rotation shaft 338 and rotatably supported by the rotation shaft 338. A worm gear 337 is formed on the outer peripheral face of the shield plate 336. A worm screw shaft 340 meshes with the worm gear 337. One end portion of the worm screw shaft 340 is drivingly coupled with a slit control motor 342. In the shield plate 336, two slits which are separated from each other in the peripheral directions, i.e., a primary (or secondary) panorama slit 344 and a primary (or secondary) CT slit 346 are formed. According to this configuration, the slit opening of the primary (or secondary) slit means 332 (or 334) can be switched by rotating the slit control motor 342 so as to move the shield plate 336 in a clockwise direction indicated by an arrow 350 or a counterclockwise direction indicated by an arrow 352. Namely, when the panorama mode is selected, the primary (or secondary) panorama slit 344 is positioned in front of the X-ray source 28 (or the image sensor 38), and, when the CT mode is selected, the primary (or secondary) CT slit 346 is positioned in front of the X-ray source 28 (or the image sensor 38). Also in the case where the thus configured primary (or secondary) slit means 332 (or 334) is used, the size of the slit opening can be automatically switched to the one corresponding to the selected imaging mode in the same manner as described above.

In the embodiment of FIG. 22, the primary and secondary CT slits 346 of the primary and secondary slit means 332, 334 are formed to be circular. In this case, X-rays which are emitted from the X-ray source and pass through the primary slit means 332 irradiate the imaging region 262 in a cone-like shape, and the imaging region 262 is formed into a spherical shape. Also when a primary CT slit having such a form is used, it is possible to conduct a desired local X-ray CT imaging.

In the above, an embodiment of a dual-purpose X-ray imaging apparatus which can conduct both the partial X-ray CT imaging and the X-ray panoramic imaging has been described. In such a dual-purpose X-ray imaging apparatus, the positioning of the chin rest 12 for the partial X-ray CT imaging may be conducted by using an X-ray panoramic image obtained in the X-ray panoramic imaging.

Figure 23:
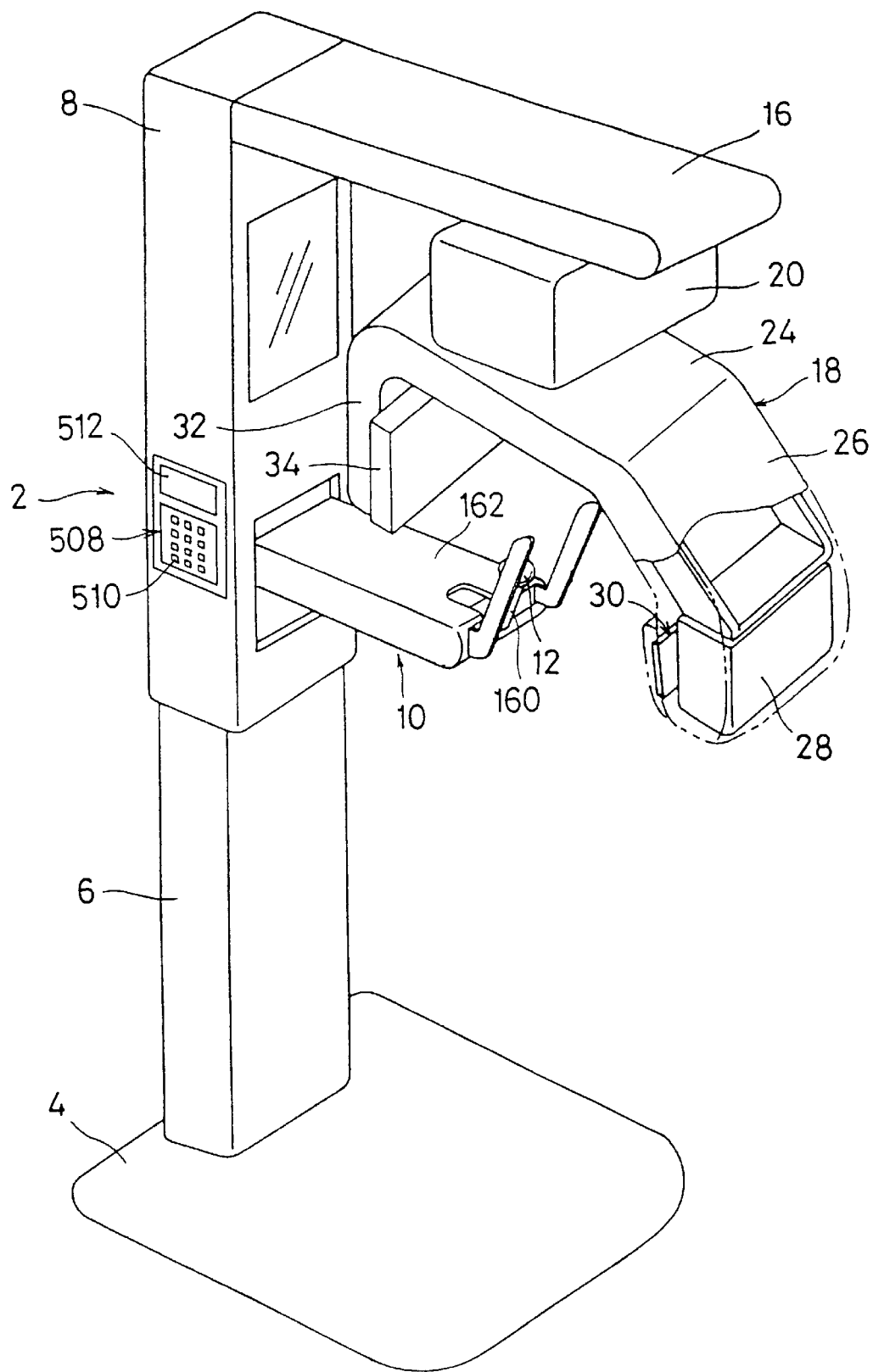
FIG. 23 is a partially cutaway perspective view showing a second embodiment of the dual-purpose X-ray imaging apparatus of the invention.
Figure 24:
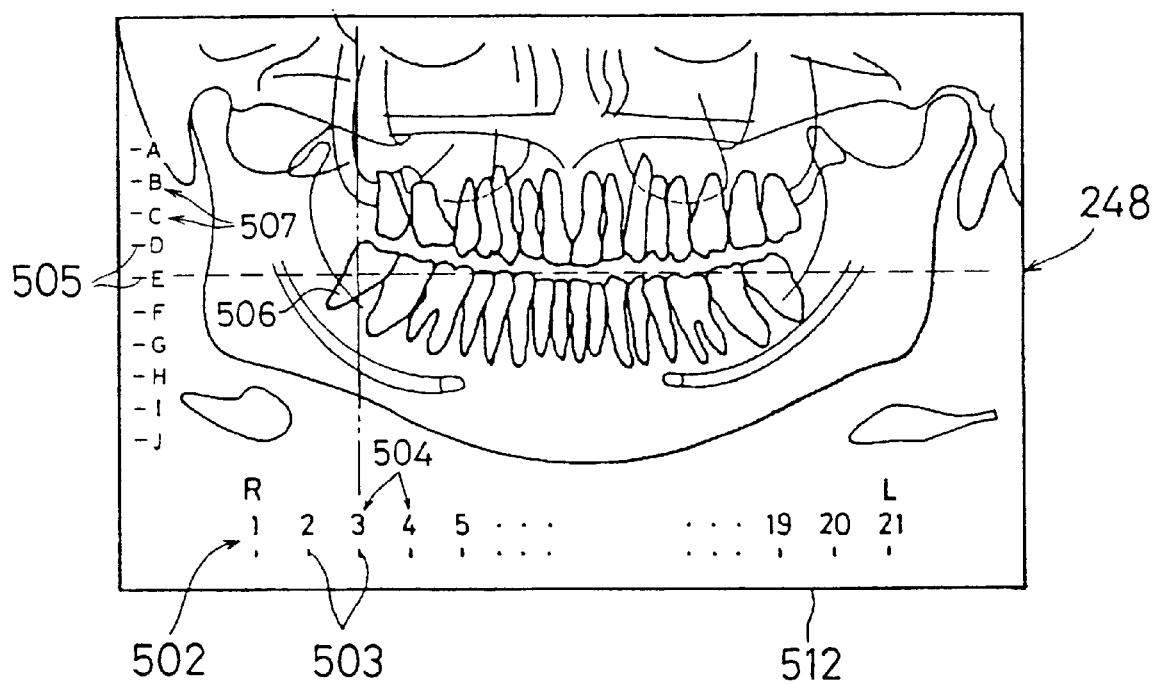
FIG. 24 is a view showing an example of a panoramic image obtained by the X-ray imaging apparatus of FIG. 23.

An X-ray imaging apparatus shown in FIG. 23 is substantially identical in fundamental configuration with the apparatuses shown in FIGS. 1 to 20 except the manner of positioning the chin rest 12 at a predetermined position. In the panoramic imaging in the X-ray imaging apparatus, as shown in FIG. 24, a panoramic image is displayed on the displaying means 248 (see FIG. 9) for displaying an X-ray image. In the image signal processing means 236, position information 502 is added to the image signal which is to be output from the processing means 236. The panoramic image containing the position information 502 is displayed on the displaying means 248. In the embodiment, the position information 502 includes scale marks 503 which are arranged from the left side of the display screen to the right side at substantially equal intervals. Numerals 504 from "1"

to "21" are added to the scale marks 503. The numbers correspond to positions in the curve of dental arch. In the position information 502, the symbol "R" indicates the right side and the symbol "L" the left side. The position information 502 includes scale marks 505 which are arranged from the upper side of the display screen to the lower side at substantially equal intervals. Symbols 507 from "A" to "J" are added to the scale marks 505.

In the case where such a panoramic image is observed and a partial X-ray CT image of, for example, a molar tooth indicated by a numeral 506 is requested, operation key means 508 disposed on the elevator frame 8 of the apparatus frame 2 shown in FIG. 23 is operated for specification. The operation key means 508 has keys 510 including operation keys for designating the maxillary teeth and the mandibular teeth, ten keys for designating a number and a symbol, and the like, and a display device 512. When one of the keys 510 is pressed, the contents of the pressed key 510 and X-ray image are displayed on the display device 512. When the molar tooth 506 is to be designated, for example, "3," "-," and "E" of the keys 510 are pressed in accordance with the coordinates 3-E displayed on the display screen 248. As a result of this pressing operations, "3-E" is displayed on the display device 512. In relation to the operation key means 508, position information storing means (not shown) for storing position information of the curve of dental arch is disposed. The chin rest 12 is positioned at the predetermined position on the basis of the position information stored in the storing means.

In the same manner as described above, this positioning is conducted by controlling the X-, Y-, and Z-axis control motors 142, 158, and 114 of the object position adjusting mechanism 10 (FIG. 1) on the basis of the read out position information. In the positioning, both the operation key means 508 and the operation panel 176 shown in FIG. 8 may be used.

Also in this configuration, in the partial X-ray CT imaging, the object can be automatically positioned in the predetermined imaging region. Particularly in an apparatus such as the embodiment in which both the partial X-ray CT imaging and the X-ray panoramic imaging are enabled, a panoramic image can be easily obtained, and hence the positioning of the object in the partial X-ray CT imaging can be conducted easily and correctly by using the panoramic image.

In the dual-purpose X-ray imaging apparatus described above, the object positioning means (in the embodiment, the chin rest 12) is mounted on the elevator frame 8 via the object position adjusting mechanism 10 so that the position of the means is adjustable in the anteroposterior, lateral, and vertical directions, and the position of the object positioning means is adjusted in accordance with the object. In these X-ray imaging apparatuses, the object position adjusting mechanism 10 may be configured in the following manner, for example. That is, in the object position adjusting mechanism 10 shown in FIG. 6, the first moving table 98 (the table which is moved in the vertical direction) may be omitted, and the position of the object positioning means may be adjusted by vertically moving the elevator frame 8 (FIG. 1). In this case, the second moving table 116 (the table which is moved in the anteroposterior direction), the third moving table 144 (the table which is moved in the lateral direction), and the vertical moving mechanism including the elevator frame 8 constitute the object position adjusting mechanism. Alternatively, the supporting means 18 may be made movable in the anteroposterior and lateral directions by using the plane moving mechanism 20 while omitting the second moving table 116 and the third moving table 144 in the object position adjusting mechanism 10 of FIG. 6. In this case, the first moving table 98 constitutes the object position adjusting mechanism, and the plane moving mechanism 20 constitutes the supporting means position adjusting mechanism which relatively moves the X-ray source 28 and the image sensor 38 with respect to the object. For an alternative to above constitutions, the supporting means 18 may be made movable in the vertical direction by using the elevating mechanism of the elevator frame 8, and in the anteroposterior and lateral directions by using the plane moving mechanism 20 while omitting the first to third moving tables 98, 116, 144. In this case, a vertical moving mechanism including the elevator frame 8 and the plane moving mechanism 20 constitute the supporting means position adjusting mechanism. According to this configuration, positioning of the object into the imaging region is enabled by using the moving mechanisms equipped in the X-ray imaging apparatus, that is the elevating mechanism of the elevator frame 8 and the plane moving mechanism 20. In that case, a detection sensor consisting of a combination of a light emitting device, and a noncontact optical ranging sensor which is called a PSD element and detects reflected light from the diseased part may be used. In the detection sensor, the optical ranging sensor measures a distance of anteroposterior direction between the apparatus frame 2 and the patient. On the basis of the measurement result, the motors of the plane moving mechanism 20 and the elevator frame 8 may be controlled so as to conduct the positioning. This system has a merit that the supporting means is moved and the patient is not required to be moved.

Figure 25:
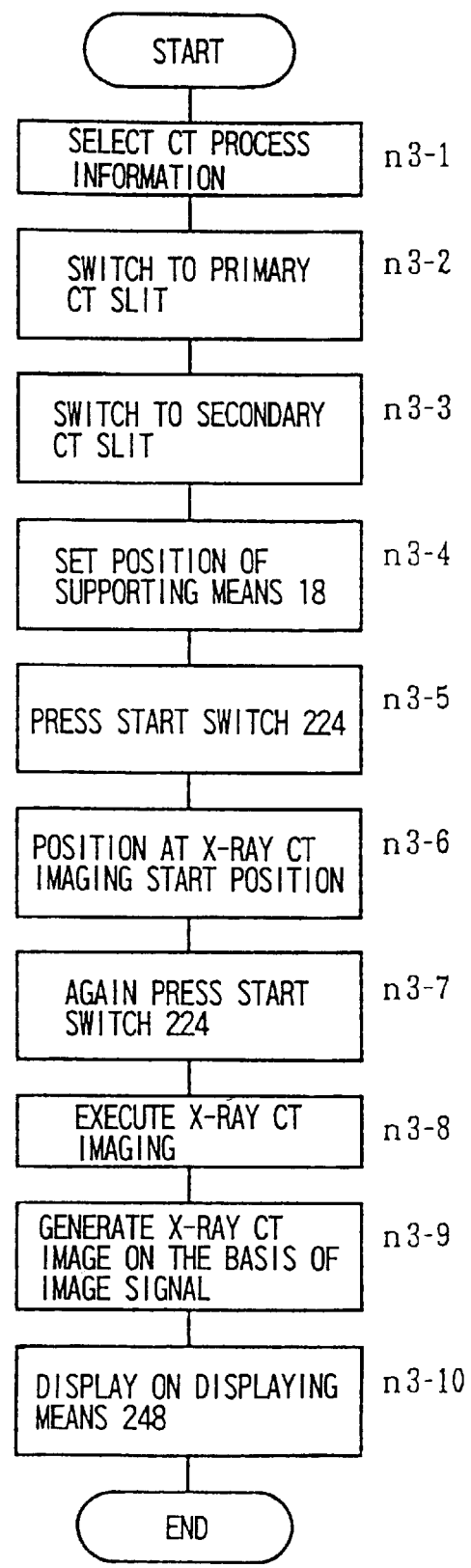
FIG. 25 is a flowchart for illustrating an imaging operation in a CT mode when a modification of object positioning means is applied to the dual-purpose X-ray imaging apparatus.

In the dual-purpose X-ray imaging apparatus comprising such a supporting means position adjusting mechanism, when the partial X-ray CT imaging is to be conducted in the CT mode, the imaging is executed in accordance with the flowchart of FIG. 25. In this case, as easily understood from a comparison between the flowcharts of FIGS. 16 and 25, the object is relatively positioned in the imaging region by, in place of the positioning of the chin rest, the positioning of the supporting means 18, i.e., the positioning of the X-ray source 28 and the image sensor 38. The positioning of the supporting means 18 can be conducted by controlling the operations of the elevation control motor 15 (see FIG. 2) which vertically moves the elevator frame 8, and the X- and Y-axis control motors 42 and 44 of the plane moving mechanism 20.

In the dual-purpose X-ray imaging apparatus, the positioning of the object positioning means may be conducted by the vertical movement of the chin rest 12 with respect to the elevator frame 8, and the anteroposterior and lateral movements of the supporting means 18 with respect to the elevator frame 8 by means of the plane moving mechanism 20.

Figure 26:
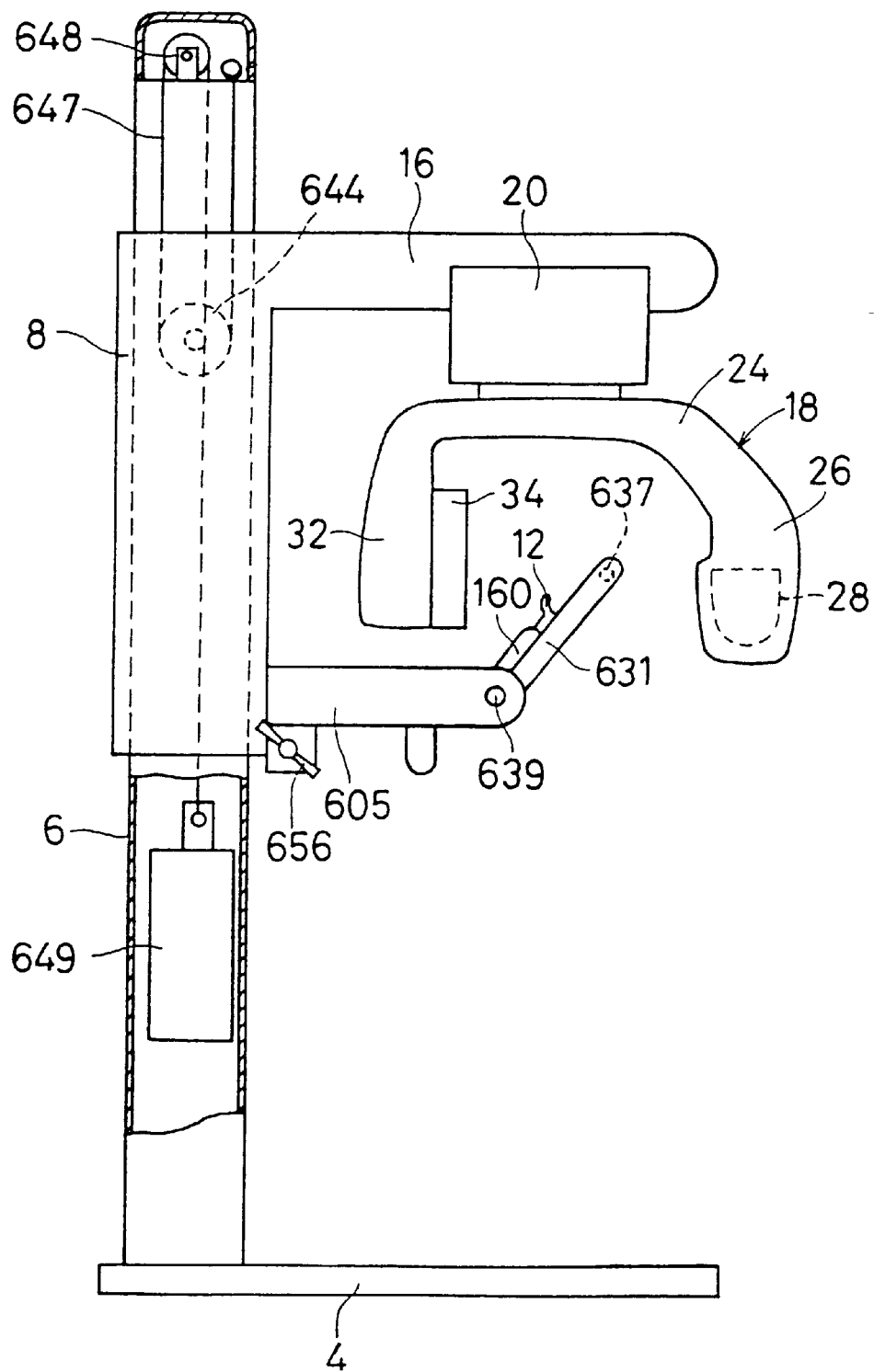
FIG. 26 is a partially cutaway side view showing the dual-purpose X-ray imaging apparatus with another modification of the object positioning means.
Figure 27:
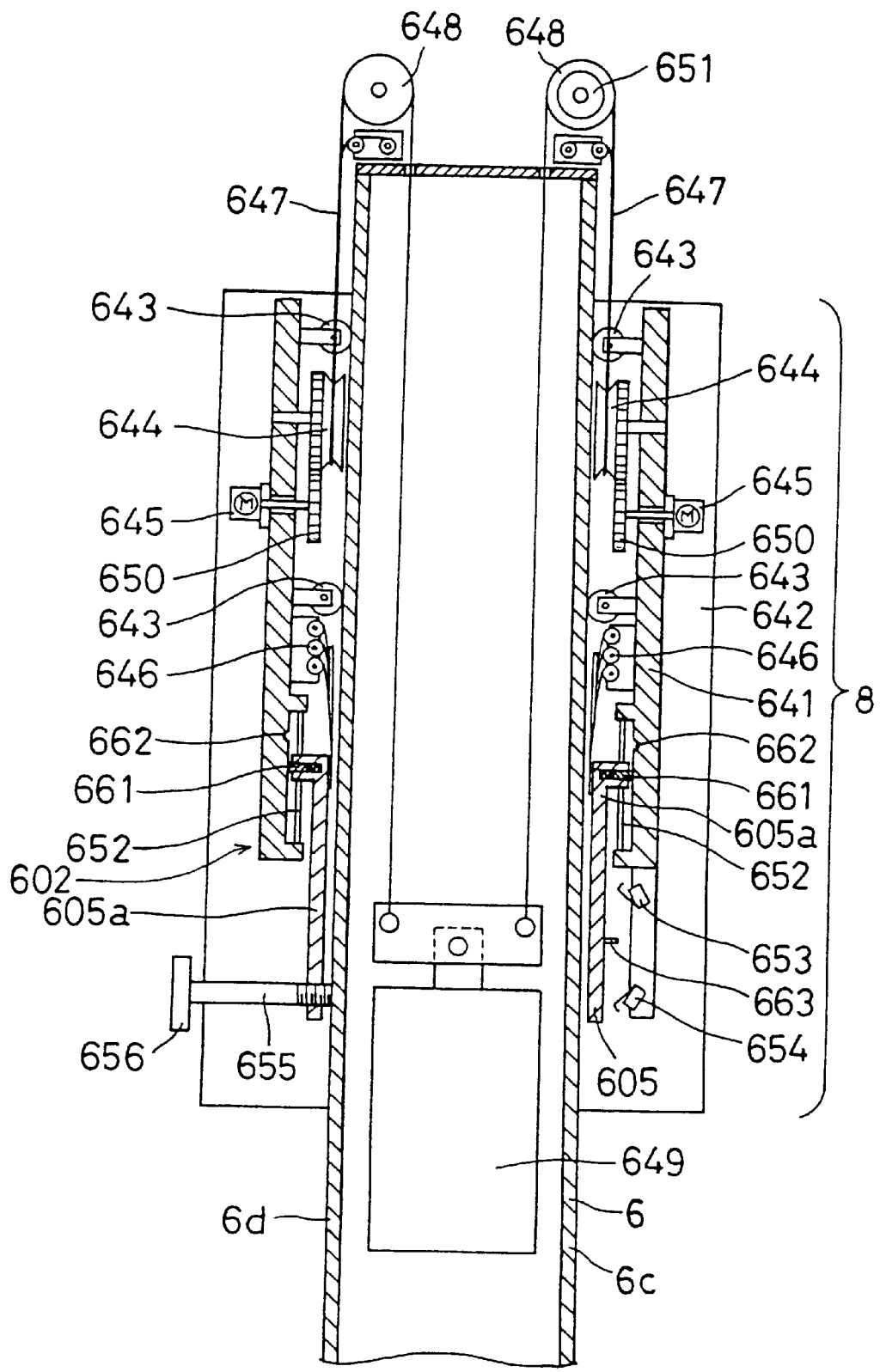
FIG. 27 is a sectional view showing an elevator frame and proximate region of the dual-purpose X-ray imaging apparatus of FIG. 26.

Referring to FIGS. 26 and 27, in the embodiment, in the same manner as the embodiments of FIGS. 1 to 20, the elevator frame 8 is mounted on the column 6 of the apparatus frame 2 so as to be movable in vertical direction, and the supporting means 18 is mounted on the elevator frame 8 via the plane moving mechanism 20 so as to be movable in anteroposterior and lateral directions.

In the embodiment, a support frame 605 is mounted on the elevator frame 8 via an object position adjusting mechanism 602 (FIG. 27) so as to be movable in vertical direction, and the chin rest 12 is mounted on the support frame 605 via the support rod 160. A pair of temporal press members 631 (only one of the members is shown in FIG. 26) are disposed on the sides of the chin rest 12, respectively. The temporal press members 631 are attached to the support frame 605 so as to be positionally adjustable. The pair of temporal press members 631 are caused to approach/separate each other by rotating a dial 639. Ear rods 637 (only one of the rods is shown in FIG. 26) are attached to the tip ends of the members, respectively.

As shown in FIG. 27, the elevator frame 8 comprises a frame body 641, a case 642, two pairs of right and left guide wheels 643 respectively disposed on the right and left sides, running blocks 644, motors 645, and constant force springs 646. The frame body 641 is formed so as to surround the column 6. The horizontal arm 16 (FIG. 26) elongates from the upper end portion of the frame body 641. Two guide wheels 643 are attached to each of inner faces of the frame body 641 which respectively oppose the side faces 6c and 6d of the column 6 so that the guide wheels 643 are slidable on the side faces 6c and 6d, whereby the elevator frame 8 is supported so as to be movable along the column 6 in vertical direction.

The running blocks 644 are disposed on the inner faces of the upper portion of the frame body 641, respectively. A wire 647 one end of which is fixed to the top of the column 6 is wound on each of the running blocks 644. Each wire 647 is wound on a standing block 648 disposed on the top of the column 6, via the running block 644. The other ends of the wires are connected to a balance weight 649. The balance weight 649 is disposed so as to be movable in the column 6 in vertical direction. The running blocks 644 mesh with gears 650 attached to the output shafts of the motors 645, respectively. Therefore, the elevator frame 8 is vertically moved by the rotation drive of the motors 645. When the frame reaches a desired vertical position, an electromagnetic brake 651 which is disposed in relation to one of the standing blocks 648 stops the rotation of the standing block 648, thereby enabling the elevator frame 8 to be stably held at a predetermined position.

A pair of guide shafts 652 elongate in the lower portion of the frame body 641 of the elevator frame 8, in parallel with the direction of the vertical movement of the elevator frame 8. The guide shafts 652 are fitted into guide holes which are formed in a pair of guide pieces 605a of the support frame 605, respectively. In this way, the support frame 605 is supported so as to be movable in vertical direction with respect to the elevator frame 8. Free ends of the constant force springs 646 attached to the frame body 641 are connected to the upper ends of the corresponding guide pieces 605a. The number of the constant force springs 646 is adequately selected in accordance with the weight of the support frame 605 to be hung. Therefore, it is easy for the operator to manually move the support frame 605 in vertical direction. The chin rest 12 and the temporal press members 631 are moved in vertical direction integrally with the support frame 605.

A positioning projection 661 opposing the inner face of the frame body 641 is attached to each of the guide pieces 605a. During the X-ray imaging process, the projections 661 are respectively fitted into positioning recesses 662 of the frame body 641, thereby positioning the support frame 605 with respect to the elevator frame 8. An abutting piece 663 is disposed on one of the guide pieces 605a. A pair of limit switches 653 and 654 are disposed on the frame body 641 so as to correspond to the abutting piece 663 and with being vertically separated from each other. The elevator frame 8 is vertically movable with respect to the support frame 605 within the range between the limit switches 653 and 654.

A stopper shaft 655 is also attached to the guide piece 605a of the support frame 605. A handle 656 is fixed to the stopper shaft 655. When the handle 656 is rotated, the stopper shaft 655 is projected or retracted with respect to the guide piece 605a. Under the projection state, the stopper shaft is frictionally pressingly contacted with the side face 6d of the column 6, so as to stop the vertical movement of the support frame 605 with respect to the column 6, whereby the support frame 605 is positioned and fixed at a predetermined position.

According to this configuration, the pair of guide shafts 652, the positioning recesses 662 of the support frame 605, the positioning projections 661 of the support frame 605, and the like function as the object position adjusting mechanism. The position adjusting mechanism enables the support frame 605 to be vertically moved with respect to the elevator frame 8. According to the above configuration, vertical positioning of the first movement table 98 of the object position adjusting mechanism 10 in FIG. 6 can be replaced by the elevating mechanism of the supporting arm 605. The plane moving mechanism 20 functions as position adjusting mechanism for supporting means. The plane moving mechanism 20 can positionally adjust the supporting means 18, i.e., the X-ray source 28 and the image sensor 38 with respect to the support frame 605 in anteroposterior and lateral directions. In such a positioning mechanism, the object can be positioned at a predetermined position by a relatively simple configuration using the plane moving mechanism 20 of the dual-purpose X-ray imaging apparatus.

In the embodiment of FIGS. 26 and 27, the supporting means 18 may be vertically moved instead of vertical movement of the chin rest 12. In such a case, either between the elevator frame 8 and the plane moving mechanism 20, or between the plane moving mechanism 20 and the supporting means 18, the vertical moving mechanism may be interposed for relative moving the two components.

In the above description, although explanation was made for a dual-purpose X-ray imaging apparatus capable of conducting a partial X-ray CT imaging and an X-ray panoramic imaging, it is also possible to construct a dedicated partial X-ray CT imaging apparatus by omitting function of conducting the X-ray panoramic imaging in the dual-purpose X-ray imaging apparatus. In such a partial X-ray CT imaging apparatus, instead of the chin rest 12 functioning as the positioning means, known members such as a bite sensor, a bite block, ear rods, or a forehead presser may be used singly or combinedly.

Figure 28:
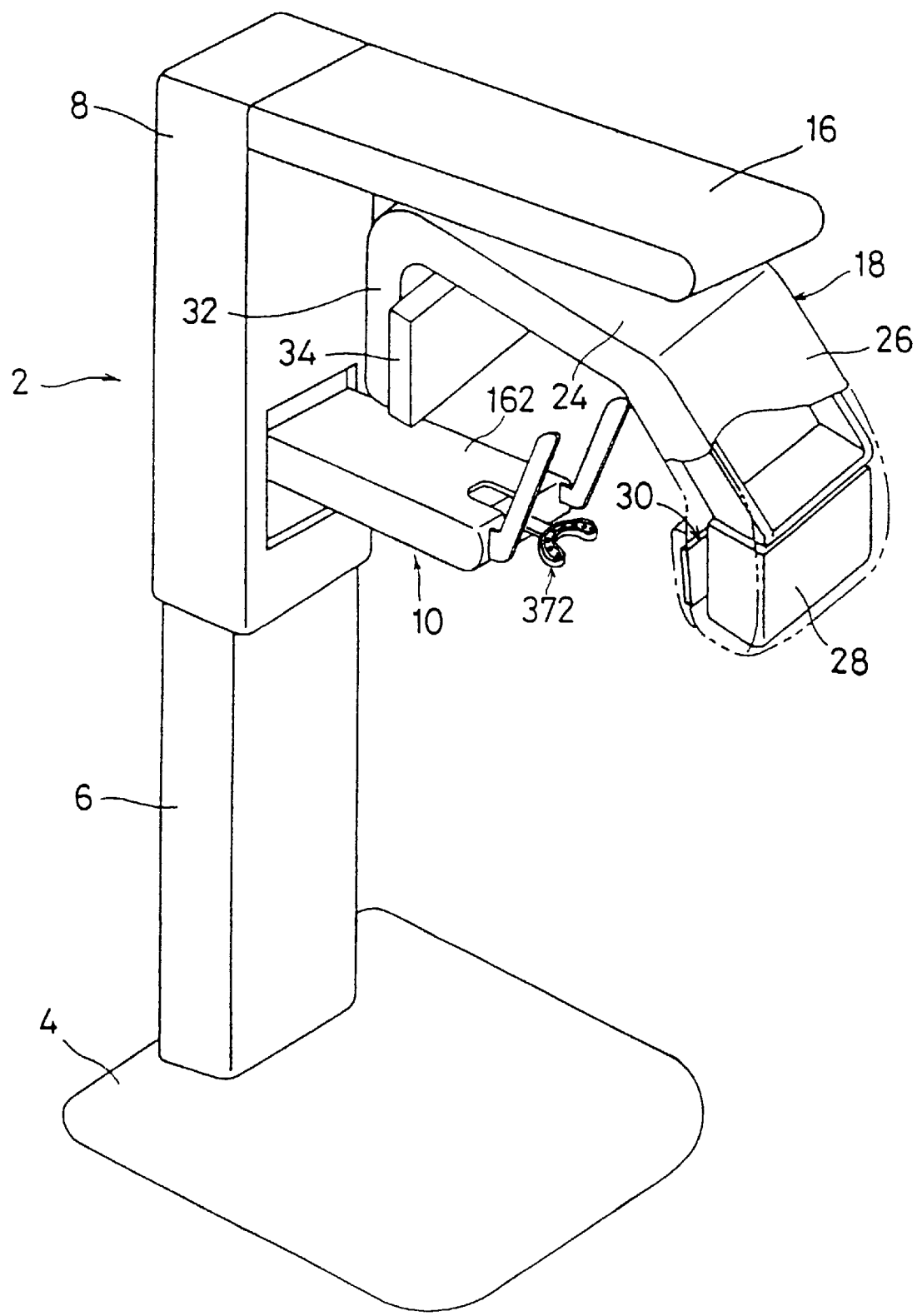
FIG. 28 is a partially cutaway perspective view showing a first embodiment of a partial CT X-ray imaging apparatus of the invention.
Figure 29:
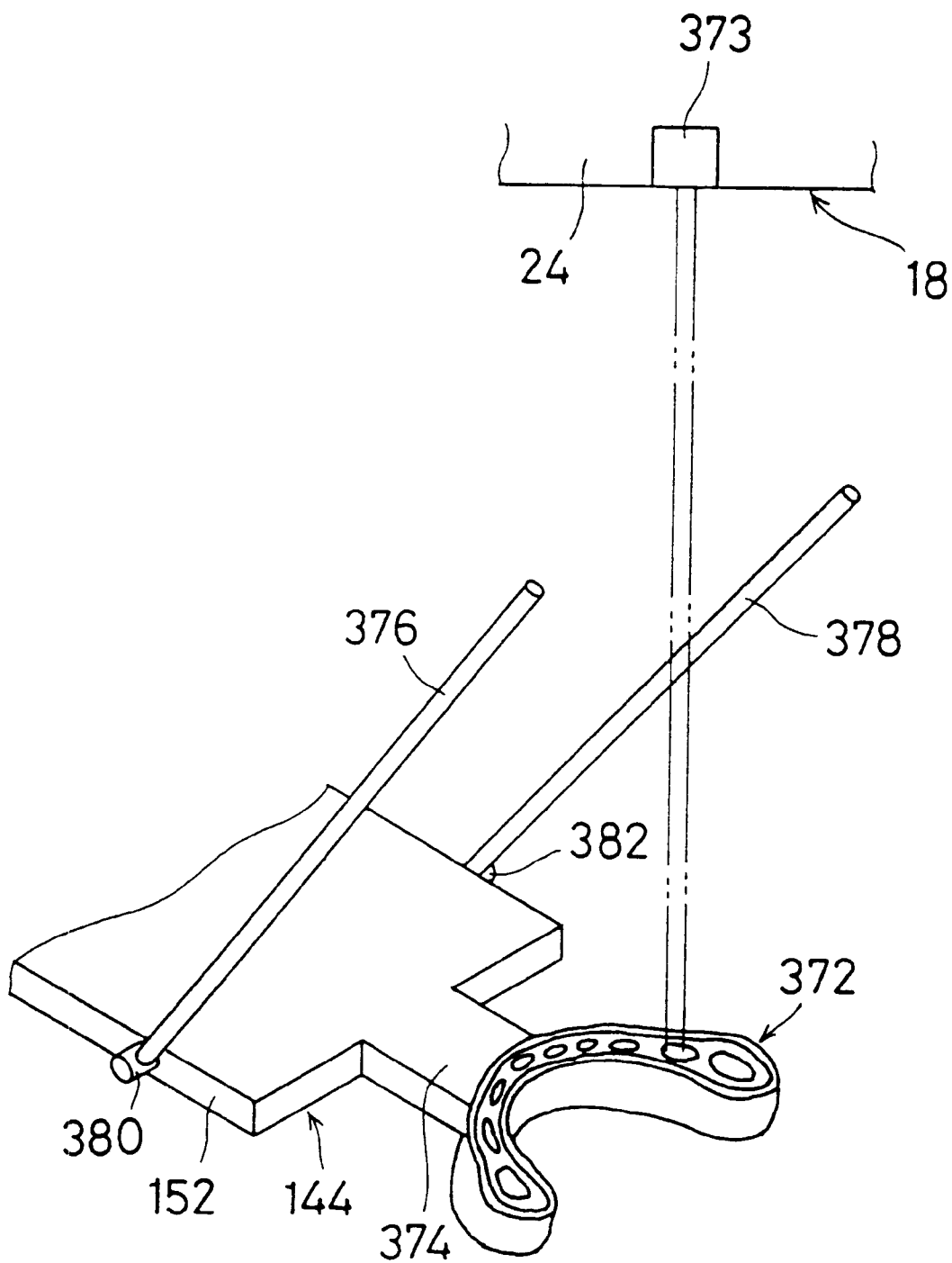
FIG. 29 is a partial perspective view showing object positioning means of the X-ray imaging apparatus of FIG. 28.

FIGS. 28 and 29 show another embodiment which uses a combination of a bite block having an impression and ear rods. In FIGS. 28 and 29, components which are identical with those of the embodiment described above are designated by the same reference numerals and their description is omitted.

Referring to FIGS. 28 and 29, in an embodiment of a specific-purpose apparatus of partial X-ray CT imaging apparatus, a bite block 372 is attached to the third moving table 144 which is supported on the apparatus frame 2 via the object position adjusting mechanism 10 having substantially same configuration as that shown in FIG. 6 so as to be movable in the anteroposterior, lateral, and vertical directions. A light beam indicator 373 is disposed on the support arm 24 which supports the X-ray source 28 and the image sensor 38 (FIG. 2). More specifically, an attachment projection 374 which is projected in the forward direction as shown FIG. 29 is formed integrally with the front end portion of the table main unit 152 of the third moving table 144 (see FIG. 6) of the object position adjusting mechanism 10. The bite block 372 which uses an impression is mounted on the tip end portion of the attachment projection 374. When the patient bites the bite block 372, the tooth form of the patient is formed. The bite block 372 may be combinedly used with ear rods 376 and 378 as required. In the same manner as the bite block 372, for example, the ear rods 376 and 378 may be disposed on the table main unit 152 in a foldable manner. In the illustrated embodiment, rod attachment members 380 and 382 are mounted on the side faces of the table main unit 152, and ends of the ear rods 376 and 378 in one side are fixed to the rod attachment members 380 and 382, respectively. The other ends of the ear rods 376 and 378 obliquely upwardly elongate, and are respectively put on the ears of the patient, whereby the head of the patient can be positioned more correctly at the predetermined position with respect to the apparatus frame 2 (FIG. 1).

The light beam indicator 373 is disposed on the rotation axis of the support arm 24 which constitutes the supporting means 18. The light beam indicator 373 may be configured by, for example, a light projecting device. As shown by a one-dot chain line in FIG. 29, a light beam from the light beam indicator 373 is projected toward the bite block 372 in a perpendicularly downward direction with substantially coinciding with the rotation axis.

In the embodiment in which the bite block 372, the ear rods 376 and 378, and the light beam indicator 373 are combinedly used, the positioning of the object is conducted in the following manner. First, the patient bites the bite block 372 to form the bite block into a shape corresponding to the tooth form of the patient. Next, the object position adjusting mechanism 10 is operated so that the light beam from the light beam indicator 373 is projected onto the site of the bite block 372 corresponding to the patient' site to be partial X-ray CT imaged, thereby positioning the bite block 372 to a predetermined position. As easily understood, the region onto which the light beam from the light beam indicator 373 is projected corresponds to the imaging region in the X-ray CT imaging. This positioning of the bite block 372 enables the site to be imaged to be correctly positioned in the imaging region. The positioning of the bite block 372 can be conducted by, for example, pressing switches which are to be manually operated, so that the X-, Y-, and Z-axis control motors 142, 158, and 114 are operated as required. Alternatively, the X-, Y-, and Z-axis control motors 142, 158, and 114 may be operated automatically.

Thereafter, the patient bites the bite block 372 which has been positioned. Since the site of the bite block 372 corresponding to the site to be imaged is at the imaging position, the operation of biting the block allows the site to be imaged to be correctly positioned in the imaging region. Then, the ear rods 376 and 378 are put on the ears of the patient so that the site is positioned more correctly at the position. In this way, in the configuration in which the bite block 372 and the light beam indicator 373 are used, the positioning can be conducted manually, easily, and correctly.

In a dedicated partial X-ray CT imaging apparatus, as easily understood, the X-ray source 28 and the image sensor 38 are required only to be rotated about the imaging region 262 (FIG. 18). As shown in FIG. 28, therefore, the plane moving mechanism may be omitted, and the support arm 24 of the supporting means 18 may be rotatably supported by the horizontal arm 16. According to this configuration, the apparatus can be simplified.

In the embodiment shown in FIGS. 28 and 29, the combination of the bite block 372 and the ear rods 376 and 378 is used. Alternatively, a combination in which a forehead presser is employed in place of the ear rods 376 and 378 may be used. A forehead presser is a member which restricts the position of the forehead of the patient biting the bite block 372, and may be disposed on, for example, the plane moving mechanism 20 (FIG. 1). Specifically, a support rod may elongate from the plane moving mechanism 20 so as to pass through an opening formed in the support arm 24, and an attachment member may be mounted on the tip end of the rod. The forehead presser may be attached to the attachment member so that the rods elongate above the bite block 372.

Figure 30:
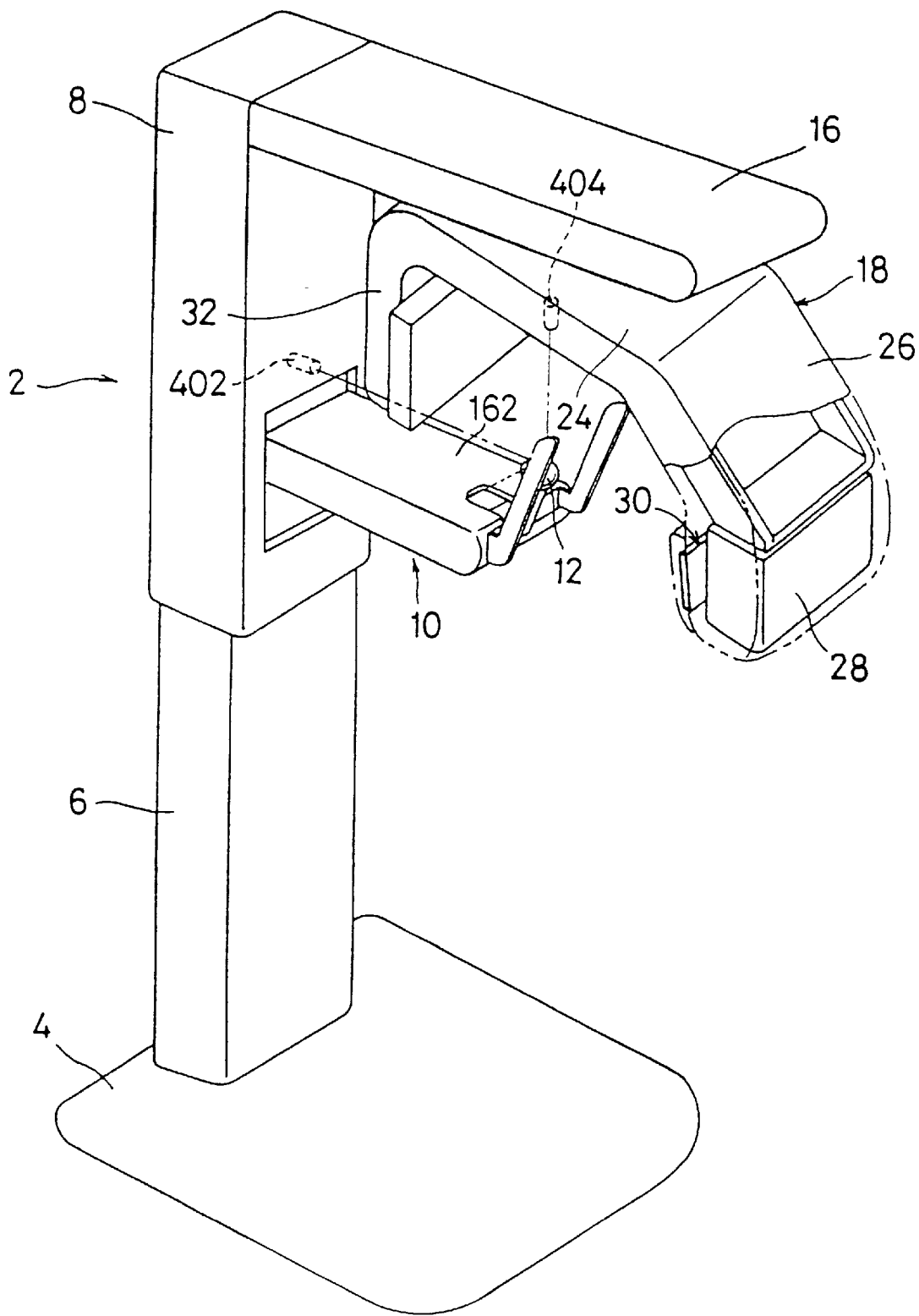
FIG. 30 is a partially cutaway perspective view showing a second embodiment of the partial X-ray CT imaging appartus of the invention.

In the embodiment, the combination of the bite block 372 and the light beam indicator 373 is used. In place of this combination, for example, a combination of a chin rest and two light beam indicators may be used as shown in FIG. 30. Referring to FIG. 30 which shows another embodiment of the partial X-ray CT imaging apparatus, one light beam indicator 402 is disposed on the front face (the left face in FIG. 30) of the elevator frame 8, and the other light beam indicator 404 is disposed on the support arm 24 which constitutes the supporting means 18. In the same manner as the embodiment of FIGS. 28 and 29, the other light beam indicator 404 is disposed on the rotation axis of the supporting means 18 and projects a light beam toward the chin rest 12 in a approximately perpendicularly downward direction which substantially coincides with the rotation axis. The light beam indicator 402 forward projects a light beam from a substantially median line of the front face toward the chin rest 12.

When the two light beam indicators 402 and 404 are used in this way, the region where the light beams from the light beam indicators 402 and 404 cross each other serves as the imaging region. Therefore, the object can be positioned in the imaging region by means of a noncontact measurement by positioning the region where the light beams from the light beam indicators 402 and 404 cross each other, at the site of the patient to be imaged under the state in which the chin is placed on the chin rest 12. In the same manner as described above, the positioning of the chin rest 12 can be conducted by controlling the X-, Y-, and Z-axis control motors 142, 158, and 114 of the object position adjusting mechanism 10 as required. For example, the positioning may be conducted by pressing switches which are to be manually operated.

In the above dual-purpose X-ray imaging apparatus and partial X-ray CT imaging apparatus having object position adjusting mechanisms and/or supporting means position adjusting mechanisms of various types are described. The dual-purpose X-ray imaging apparatus and partial X-ray CT imaging apparatus, however, are preferably constituted such that relative positions between the object positioning means (e.g. chin rest), and the X-ray source and the image sensor are adjusted as follows in view of functional characteristics and manufacturing cost of respective apparatuses.

In the dual-purpose X-ray imaging apparatus, since the plane moving mechanism is required for conducting the X-ray panoramic imaging, a most preferable positioning mechanism is of a type that the supporting means is moved in the anteroposterior and vertical directions by means of the plane moving mechanism while the object positioning means is moved in the vertical direction by means of the object position adjusting mechanism (the same mechanism as the object position adjusting mechanism of FIG. 6 except that the second and third moving tables are omitted). A second-preferable positioning mechanism is of a type that, as shown in FIGS. 26 and 27, the supporting means is moved in the anteroposterior and lateral directions by means of the plane moving mechanism while the support frame provided with the object positioning means is moved in the vertical direction by means of the object position adjusting mechanism. A third-preferable positioning mechanism is of a type that, in the case of applying as the plane moving mechanism a laminate forming mechanism using well known curved slot or the like other than the X-Y table, the supporting is moved in the anteroposterior and lateral directions during the panoramic imaging process, while the object positioning means is moved in the anteroposterior, lateral, and vertical directions by means of the object position adjusting mechanism shown in FIG. 6 without using the plane moving mechanism during the CT imaging process. Among other preferable positioning mechanisms, there is a mechanism of such a type that the Z-axis table and the Z-axis control motor is added to the plane moving mechanism, for example.

On the other hand, since the partial X-ray CT imaging apparatus essentially requires no the plane moving mechanism, a most preferable positioning mechanism is of a type that the object positioning means is moved in the anteroposterior, lateral, and vertical directions by means of the object position adjusting mechanism shown in FIG. 6. A second-preferable positioning mechanism is of a type that the partial X-ray CT imaging apparatus is additionally provided with a plane moving mechanism, and the supporting means is moved in the anteroposterior and lateral directions by using the plane moving mechanism, while the object positioning means is moved in the vertical direction by means of object position adjusting mechanism (the same mechanism as the object position adjusting mechanism of FIG. 6 except that the second and third moving tables are omitted). A third-preferable mechanism is of a type that, as shown in FIGS. 26 and 27, the supporting means is moved by means of the plane moving mechanism, while the support frame is moved by means of the object position adjusting mechanism.

In the embodiments of the dual-purpose X-ray imaging apparatus and dedicated X-ray imaging apparatus described above, a MOS sensor is used as the image sensor 38 which is one kind of the X-ray imaging means. In place of the MOS sensor, a sensor of another kind such as a CCD sensor, an X.I.I. (X-ray image intensifier), an X.I. CCD camera (X-ray intensified CCD camera), an X-ray solid state device consisting of thin film field effect transistors (FETs) or the like may be used.

In the embodiments described above, a sensor which obtains X-ray image information in the form of an electric signal, or the like is used as the X-ray imaging means. For the panoramic imaging, a conventional X-ray film may be used. In the case where an X-ray film is used, the X-ray imaging means further comprises an X-ray film cassette which houses an X-ray film, and a film transporting motor which transports the film cassette in a direction perpendicular to X-ray beams.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A partial X-ray CT imaging apparatus comprising:
an X-ray source for generating X-rays;
X-ray imaging means for detecting X-rays having passed through an object;
supporting means for supporting the X-ray source and the X-ray imaging means so that the X-ray source and the X-ray imaging means are opposed to each other across the object;
an apparatus frame for supporting the supporting means so as to be rotatable about a rotation axis; and
rotation driving means for rotating the supporting means with respect to the apparatus frame; and wherein
an image region according to the X-ray source and the X-ray imaging means is substantially positioned on an extension line of the rotation axis of the supporting means;
during a partial X-ray CT imaging process, the rotation driving means rotates the supporting means in a predetermined direction about the rotation axis, and the X-ray source and the X-ray imaging means are revolved about the imaging region, thereby conducting a partial CT imaging of the object;
the supporting means comprises a light beam indicator for projecting a light beam toward the object positioning means; and
the light beam indicator is disposed on the rotation axis for the supporting means.

2. An X-ray imaging apparatus comprising:
an X-ray source for generating X-rays;
X-ray imaging means for detecting X-rays having passed through an object;
supporting means for supporting the X-ray source and the X-ray imaging means so that the X-ray source and the X-ray imaging means are opposed to each other across the object;
an apparatus frame for supporting the supporting means; and
moving means moving the supporting means with respect to the apparatus frame;
the X-ray imaging apparatus further comprising mode switching means for switching between a CT mode in which a partial CT image is generated, and a panorama mode in which a panoramic tomographic image is generated; and wherein
when the CT mode is selected by the mode switching means, the moving means moves the X-ray source and the X-ray imaging means along a CT image formation locus during a partial CT imaging process, and when the panorama mode is selected by the mode switching means, the moving means moves the X-ray source and the X-ray imaging means along a panoramic image formation locus during a panoramic imaging process; and
the CT image formation locus is a locus in which the supporting means is rotated about a rotation axis of the supporting means without moving the rotation axis, the panoramic image formation locus is a locus in which the rotation axis of the supporting means is moved along an envelope and the supporting means is rotated about the rotation axis as required, and, when the X-ray source and the X-ray imaging means are moved along the panoramic image formation locus, X-rays emitted from the X-ray source toward the X-ray imaging means are irradiated along a dental arch.

3. The X-ray imaging apparatus of claim 2 further comprising movement controlling means for controlling the moving means,
wherein the movement controlling means controls an operation of the moving means so that in the CT mode the X-ray source and the X-ray imaging means are moved along the CT image formation locus, and in the panorama mode the X-ray source and the X-ray imaging means are moved along the panoramic image formation locus.

4. The X-ray imaging apparatus of claim 3, wherein the moving means comprises:

an X-axis control motor for moving the supporting means in an anteroposterior direction;

a Y-axis control motor for moving the supporting means in a lateral direction; and a rotation control motor for rotating the supporting means about a rotation axis, wherein the movement controlling means, controls an operation of the rotation control motor in the CT mode, and simultaneously controls operations of the X-axis control motor, the Y-axis control motor, and the rotation control motor in the panorama mode.

5. The X-ray imaging apparatus of claim 3, wherein the X-ray imaging means detects the X-rays from the X-ray source and outputs an image signal, the X-ray imaging apparatus further comprising, in relation to the X-ray imaging means, image signal processing means for forming a tomographic image on the basis of the image signal, wherein the image signal processing means generates, in the CT mode, a partial CT image on the basis of the image signal from the X-ray imaging means, and, in the panorama mode, a panoramic tomographic image on the basis of the image signal from the X-ray imaging means.

6. The X-ray imaging apparatus of claim 5 further comprising, in relation to the movement controlling means and the image signal processing means, process information storing means for storing CT process information for obtaining the partial CT image and panorama process information for obtaining the panoramic tomographic image, wherein when the CT mode is selected by the mode switching means, the CT process information of the process information storing means is selected, the movement controlling means moves the X-ray source and the X-ray imaging means along the CT image formation locus on the basis of the CT process information, and the image signal processing means generates the partial CT image on the basis of the image signal from the X-ray imaging means; and, when the panorama mode is selected by the mode switching means, the panorama process information of the process information storing means is selected, the movement controlling means moves the X-ray source and the X-ray imaging means along the panoramic image formation locus on the basis of the panorama process information, and the image signal processing means generates the panoramic tomographic image on the basis of the image signal from the X-ray imaging means.

7. An X-ray imaging apparatus comprising:

an X-ray source for generating X-rays;

X-ray imaging means for detecting X-rays having passed through an object;

supporting means for supporting the X-ray source and the X-ray imaging means so that the X-ray source and the X-ray imaging means are opposed to each other across the object;

an apparatus frame for supporting the supporting means;

moving means moving the supporting means with respect to the apparatus frame;

primary slit means for restricting a range of X-rays emitted from the X-ray source toward the object, the primary slit means having primary slit switching means for switching between a primary CT slit and a primary panorama slit; and secondary slit means for restricting a range of X-rays entering the X-ray imaging means, the secondary slit means having secondary slit switching means for switching between a secondary CT slit and a secondary panorama slit;

mode switching means for switching between a CT mode in which a partial CT image is generated, and a panorama mode in which a panoramic tomographic image is generated; and wherein when the CT mode is selected by the mode switching means, the moving means moves the X-ray source and the X-ray imaging means along a CT image formation locus during a partial CT imaging process, and when the panorama mode is selected by the mode switching means, the moving means moves the X-ray source and the X-ray imaging means along a panoramic image formation locus during a panoramic imaging process;

when the CT mode is selected by the mode switching means, the primary CT slit is selected by the primary-slit switching means and the secondary CT slit is selected by the secondary-slit switching means; and when the panorama mode is selected by the mode switching means, the primary panorama slit is selected by the primary-slit switching means and the secondary panorama slit is selected by the secondary-slit switching means.

8. The X-ray imaging apparatus of claim 2 further comprising object positioning means for positioning the object in an imaging region which is between the X-ray source and the X-ray imaging means, wherein positional relationships between the object positioning means, and the X-ray source and the X-ray imaging means are relatively adjustable in anteroposterior, lateral, and vertical directions.

9. The X-ray imaging apparatus of claim 8, wherein the moving means includes a plane moving mechanism for supporting the supporting means in a manner that the supporting means is movable with respect to the apparatus frame in anteroposterior and lateral directions, the object positioning means is mounted on the apparatus frame via an object position adjusting mechanism for supporting the object positioning means in a manner that the object positioning means is movable in vertical directions, and positional relationships between the object positioning means, and the X-ray source and the X-ray imaging means are adjusted by the plane moving mechanism and the object position adjusting mechanism in anteroposterior, lateral, and vertical directions.

10. The X-ray imaging apparatus of claim 8, wherein positional relationships between the object positioning means, and the X-ray source and the X-ray imaging means in the CT mode are set on the basis of position information obtained from the panoramic tomographic image which is obtained in the panorama mode.

11. An X-ray imaging apparatus comprising:

an X-ray source for generating X-rays;

X-ray imaging means for detecting X-rays having passed through an object;

supporting means for supporting the X-ray source and the X-ray imaging means so that the X-ray source and the X-ray imaging means are opposed to each other across the object;

an apparatus frame for supporting the supporting means; and moving means moving the supporting means with respect to the apparatus frame;

the X-ray imaging apparatus further comprising mode switching means for switching between a CT mode in which a partial CT image is generated, and a panorama mode in which a panoramic tomographic image is generated; and wherein when the CT mode is selected by the mode switching means, the moving means moves the X-ray source and the X-ray imaging means along a CT image formation locus during a partial CT imaging process, and when the panorama mode is selected by the mode switching means, the moving means moves the X-ray source and the X-ray imaging means along a panoramic image formation locus during a panoramic imaging process; and before and after the partial CT imaging process, the supporting means is positioned at a specific angular position where a line connecting the X-ray source and the X-ray imaging means laterally elongates.

12. A partial X-ray CT imaging apparatus comprising:

an X-ray source for generating X-rays;

X-ray imaging means for detecting X-rays having passed through an object;

supporting means for supporting the X-ray source and the X-ray imaging means so that the X-ray source and the X-ray imaging means are opposed to each other across the object;

an apparatus frame for supporting the supporting means so as to be rotatable about a rotation axis;

rotation driving means for rotating the supporting means with respect to the apparatus frame;

object positioning means for positioning the object in the imaging region, disposed between the X-ray source and the X-ray imaging means; and wherein an image region according to the X-ray source and the X-ray imaging means is substantially positioned on an extension line of the rotation axis of the supporting means;

during a partial X-ray CT imaging process, the rotation driving means rotates the supporting means in a predetermined direction about the rotation axis, and the X-ray source and the X-ray imaging means are revolved about the imaging region, thereby conducting a partial CT imaging of the object;

the object positioning means is mounted on the apparatus frame via an object position adjusting mechanism; and the object positioning means is made positionally adjustable with respect to the apparatus frame by the object position adjusting mechanism in anteroposterior, lateral, and vertical directions.

13. The partial X-ray CT imaging apparatus of claim 12 further comprising:

position storing means for storing object position information relating to positional relationships between the X-ray source and the X-ray imaging means, and the object positioning means; and position selecting means for selecting object position information stored in the position storing means, wherein the X-ray source, the X-ray imaging means, and the object positioning means are held in selected positional relationships on the basis of the object position information selected by the position selecting means.

14. A partial X-ray CT imaging apparatus comprising:

an X-ray source for generating X-rays;

X-ray imaging means for detecting X-rays having passed through an object;

supporting means for supporting the X-ray source and the X-ray imaging means so that the X-ray source and the X-ray imaging means are opposed to each other across the object;

an apparatus frame for supporting the supporting means so as to be rotatable about a rotation axis; and rotation driving means for rotating the supporting means with respect to the apparatus frame; and wherein an image region according to the X-ray source and the X-ray imaging means is substantially positioned on an extension line of the rotation axis of the supporting means;

during a partial X-ray CT imaging process, the rotation driving means rotates the supporting means in a predetermined direction about the rotation axis, and the X-ray source and the X-ray imaging means are revolved about the imaging region, thereby conducting a partial CT imaging of the object;

the supporting means comprises:
a support arm which is supported by the apparatus frame so as to be rotatable about the rotation axis extending in a vertical direction;
a first attaching portion which downwardly elongates is disposed at one end portion of the support arm, and a second attaching portion which downwardly elongates is disposed at another end portion of the support arm;
the X-ray source is attached to the first attaching portion;
the X-ray imaging means is attached to the second attaching portion; and
the image region is placed between the first attaching portion and the second attaching portion of the supporting arm; and
before and after the partial CT imaging process, the support arm is positioned at a specific angular position where a line connecting the X-ray source and the X-ray imaging means laterally elongates.

15. The partial X-ray CT imaging apparatus of claim 14, wherein the X-ray source is provided with primary slit means, X-rays emitted from the X-ray source are irradiated in a cone-like shape or a pyramid-like shape through the primary slit means toward the imaging region, and the imaging region has a spherical or cylindrical shape which is substantially centered at the rotation axis of the supporting means.

* * * * *